United States Patent [19]

Van Dijl et al.

[11] Patent Number: 5,246,838
[45] Date of Patent: Sep. 21, 1993

[54] PROCESSING OF PROTEINS

[75] Inventors: Jan M. Van Dijl; Hilde E. Smith, both of Groningen; Sierd Bron, Haren; Wilhelmus J. Quax, Voorschoten; Gerard Venema, Haren, all of Netherlands

[73] Assignee: Gist-brocades, N.V., Delft, Netherlands

[21] Appl. No.: 662,005

[22] Filed: Feb. 28, 1991

[30] Foreign Application Priority Data

Feb. 28, 1990 [EP] European Pat. Off. ......... 90200477.9
Dec. 24, 1990 [EP] European Pat. Off. ......... 90203509.6

[51] Int. Cl.$^5$ .................. C12P 21/06; C12N 1/21; C12N 15/57; C07H 21/04
[52] U.S. Cl. ................. 435/69.1; 435/252.3; 435/71.2; 435/320.1; 435/220; 435/221; 435/222; 435/172.3; 536/23.2; 935/14; 935/51; 935/72
[58] Field of Search ................. 536/27, 71.1; 435/252.8, 252.9, 220, 221, 222, 252.3, 252.31, 69.1

[56] References Cited

PUBLICATIONS

Van Dijl, J. M. et al. (1990) Mol. Gen. Genet. 223 233–240.
Isaki, L. et al (A) (1990) J. Bacteriol 172:6512–6517.
Isaki, L. et al (B) (1990) J. Bacteriol. 172:469–472.
Anba, J. et al (1986) J. Gen. Microbiol. 132:689–696.
Palva, "Engineering for Secretion of Proteins by Bacteria", pp. 255–269, *Microbial Products: New Approaches* 44th Symposium of the Society for General Microbiology, (1989) S. Baumberg, I. Hunter, and M. Rhodes, eds., Cambridge University Press, Cambridge, United Kingdom.
Kawamura et al., *J. Bacteriol.* (1984) 160:442–444.
Fahnestock et al., *Appl. Environ. Microbiol.* (1987) 53:379–384.
Sloma et al., *J. Bacteriol.* (1988) 170:5557–5563.
Tokunaga et al., *J. Biol. Chem.* (1982) 257:9922–9925.
Yamada et al., *FEBS Letters* (1984) 166:179–182.
Yamagata et al., *J. Bacteriol.* (1982) 152:1163–1168.
Date et al., *Proc. Natl. Acad. Sci.* (1981) 78:6106–6110.
Wolfe et al., *J. Biol. Chem* (1983) 258:12073–12080.
Dalbey et al., *J. Biol. Chem.* (1985) 260:15925–15931.
Lampen et al., *Microbiol.* (1986) pp. 279–282.

*Primary Examiner*—Robert A. Wax
*Assistant Examiner*—G. E. Bugaisky
*Attorney, Agent, or Firm*—Morrison & Foerster

[57] ABSTRACT

The subject invention describes the cloning and overexpression of leader peptidase genes. A method for isolating a leader peptidase gene is disclosed. Overexpression of the signal peptidase in a suitable host species leads to an enhanced rate of protein processing.

6 Claims, 17 Drawing Sheets

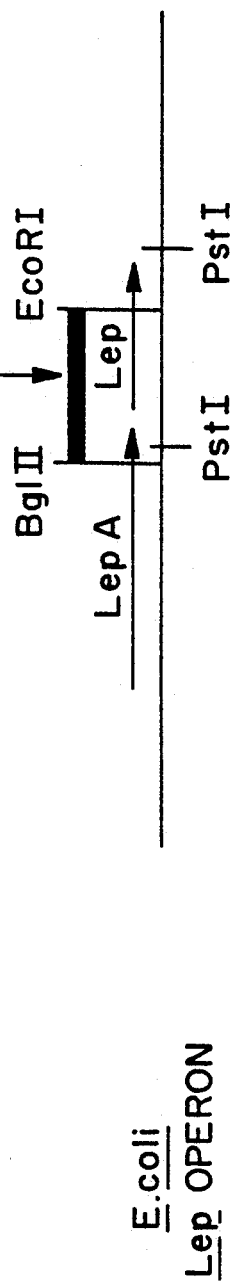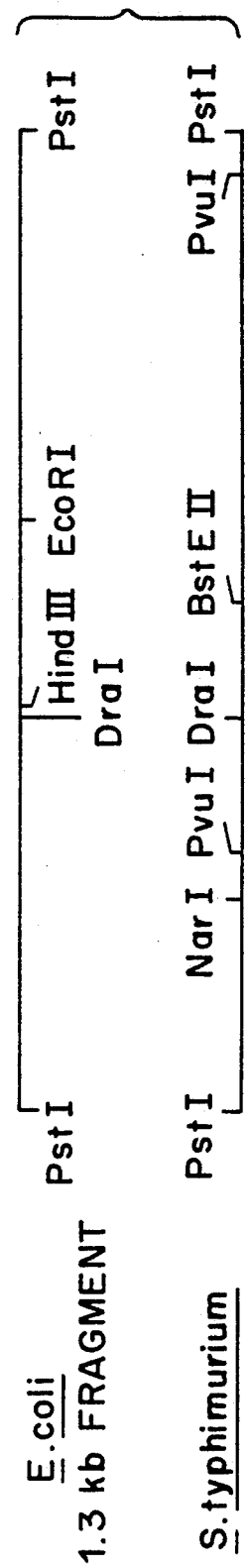
FIG. 3A
FIG. 3B 1   2   3

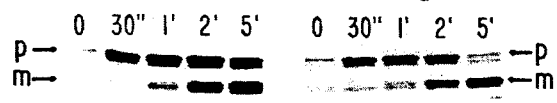
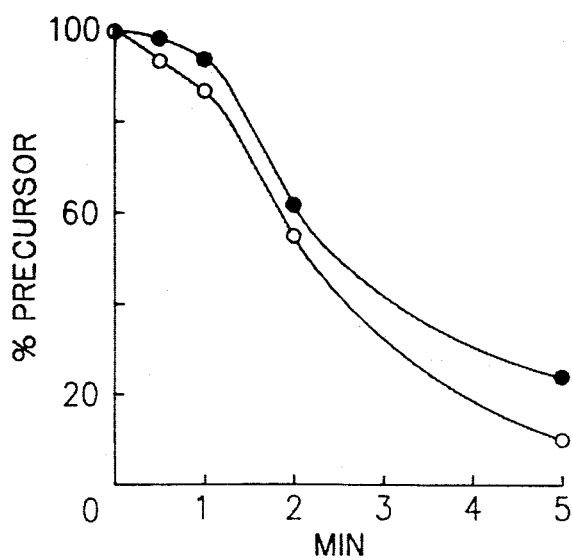
FIG. 13C
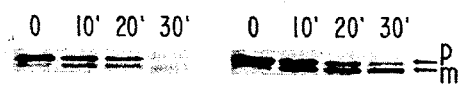
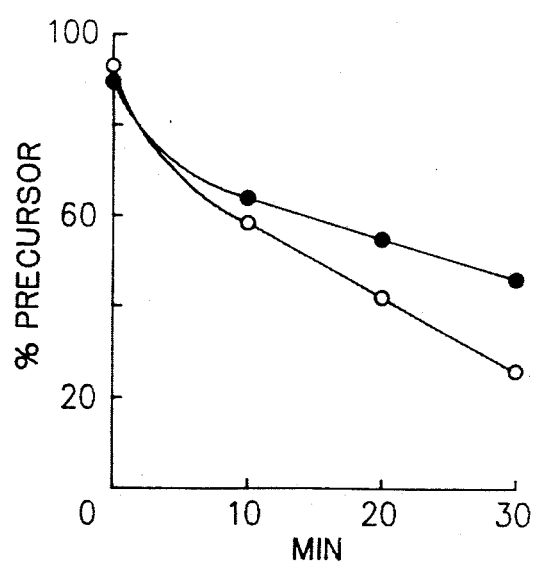
FIG. 14C

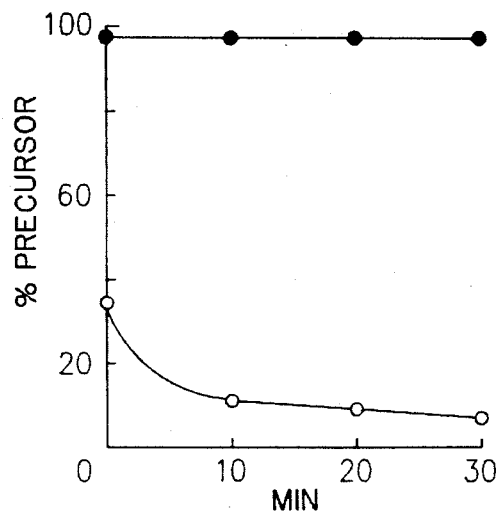
FIG. 15A  FIG. 15B
FIG. 15C
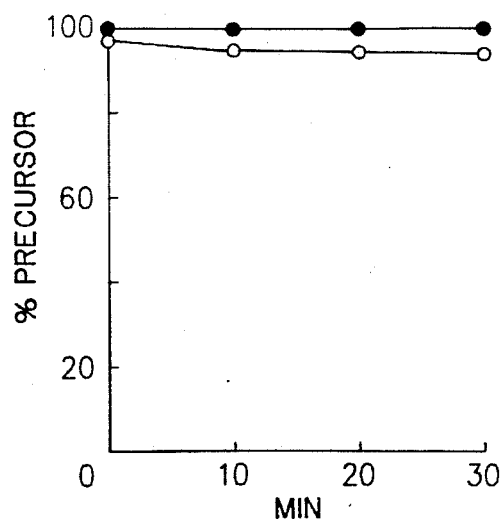
FIG. 16A  FIG. 16B
FIG. 16C

Lep B.S.   4   ENVSKKKSILEWAKAIVIAVVLALLIRNFIFAPYVVDGDSMYPTLHNRER   53
Lep E.c   67   KKVAPKPGWLETGASVFPVLAIVLIVRSFIYEPFQIPSGSMMPTLLIGDF   116

54   VFVN..........MTVKYIGEFDRGDIVVL...NGDDVHYVKRIIGL    88
         117   ILVEKFAYGIKDPIYQKTLIENGHPKRGDIVVFKYPEDPKLDYIKRAVGL   166

89   PGDTV..EMKNDQLYI.........................N    103
         167   PGDKVTYDPVSKELTIQPGCSSGQACENALPATYSNVEPSDFVQTFSRRN   216

104   GKKVDEPYLAANKKRAKQDG..........................    123
         217   GGEATSGFFEVPKNETKENGIRLSERKETLGDVTHRILTVPIAQDQVGMY   266

124   FDHLTDDFGPVKVPDNKYFVMGDNRRNSMDSRNGLGLFTKKQIAGTSKFV   173
         267   YQQPGQQLATWIVPPGQYFMMGDNRDNSADSRY.WGFVPEANLVGRATAI   315

174   FYPFN...EMRKTN   184
         316   WMSFDKQEGEWPTG   329

FIG. 17

```
BSLEP    LALLI  RNFIFAPYVVD  GDSMYPTL  HNRERVFVNMTVKYIGEFD............  RGDIVVL
ECLEP    IVLIV  RSFIYEPFQIP  SGSMMPTL  LIGDFILVEKFAYGIKDPIYQKTLIENGHPK  RGDIVVF
STLEP    IVLIV  RSFLYEPFQIP  SGSMMPTL  LIGDFILVEKFAYGIKDPIYQKTLIETGHPK  RGDIVVF
SEC11    IVVVL  ...........  SGSMEPAF  Q..............................  RGDILFL
21K      IVVVL  ...........  SGSMEPAF  H..............................  RGDLLFL
```

FIG. 21

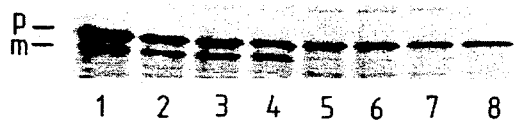
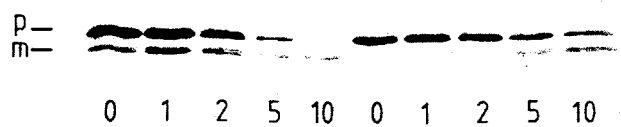
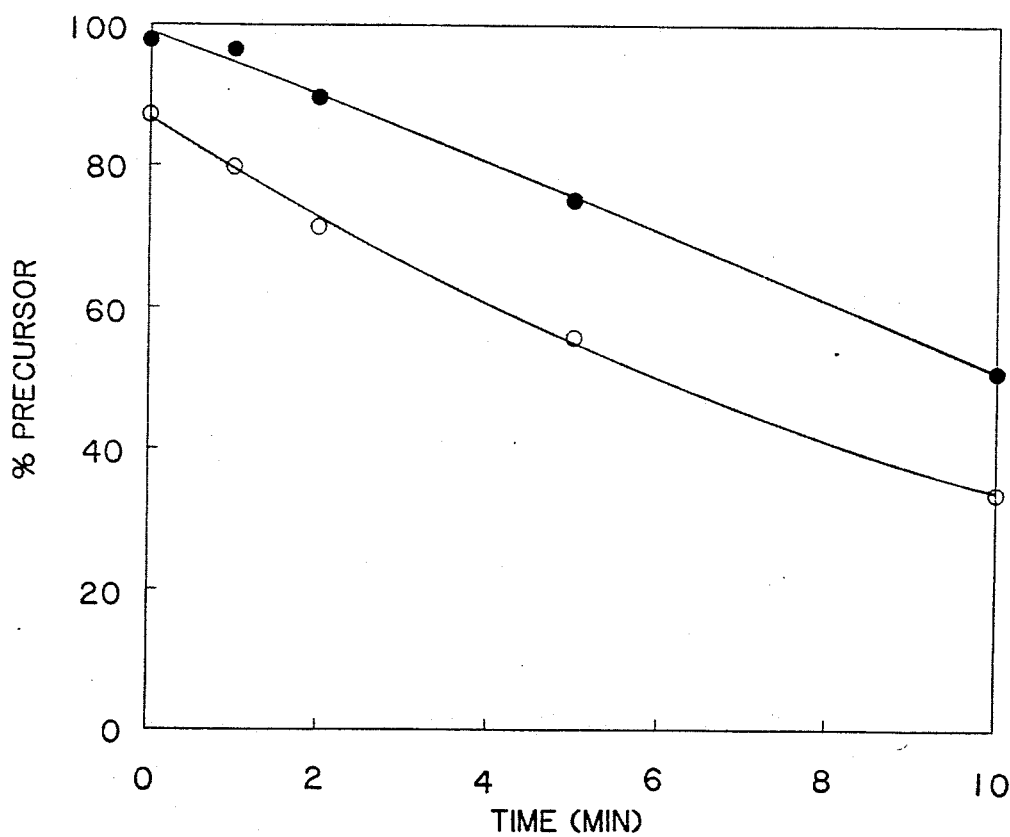
FIG. 20E

PROCESSING OF PROTEINS

TECHNICAL FIELD

The present invention relates to the microbiological production of proteins. Specifically, it relates to enzymes involved in the processing of proteins and to methods for obtaining the genes encoding said enzymes. It also relates to methods for culturing organisms wherein said genes are overexpressed. Specifically, this invention relates to the processing of exported proteins. More specifically, this invention relates to the cloning and expression of signal peptidases.

BACKGROUND OF THE INVENTION

To date the production of the majority of recombinant proteins is performed intracellularly in E.coli. To obtain the product in a usable form one has first to disrupt the cells and then to perform elaborate purification.

The purification can be greatly simplified by using a host/gene combination that leads to secretion of the expressed protein product. E.coli has often been the microorganism of choice. Since not many proteins are known to be naturally secreted by Gram-negative bacteria there is a tendency to start using Gram-positive bacteria such as Bacilli in the production of foreign proteins.

Expression levels of proteins bound to be secreted and originating from Gram-positive bacteria in both homologous and non-homologous Gram-positive hosts have often been satisfactory, yielding about 0.5–1 g/l of protein. However, yields in Gram-positive hosts are substantially lower upon expression of secretory or exported proteins from Gram-negative bacterial or eukaryotic Origin (Palva 1989). Different explanations have been given for this phenomenon and attempts have been made to enhance the yields of foreign proteins.

A primary reason for the low yields was assumed to be the extracellular proteolysis of the expression products. Much effort has therefore been spent on constructing protease-negative hosts (Kawamura and Doi 1984, Fahnestock and Fisher 1987, Sloma et al. 1988), the secretion problems however, partly remained.

Another explanation for the low yields upon expression of foreign proteins may be a rate-limiting step in the intracellular processing. The effect of such a rate-limiting step will be more pronounced if the foreign protein is overexpressed. Generally, either homologous or heterologous genes are introduced into the host cell on high copy number cloning vehicles or integrated into the genome. A strong promoter is cloned upstream of the gene or the gene is integrated downstream of a strong promoter. The introduction of such a construct may give rise to a heavy burden on the translational or secretional apparatus of the cells. Possible rate-limiting steps may be, for example, transcription, translation, intracellular transport, translocation and finally the actual release into the culture medium. Translocation and the actual release into the medium are the subject of the present invention. An important role in membrane transport of proteins is played by specific sequences in the protein.

Many secreted and membrane bound proteins are synthesized in a precursor form. This precursor contains an N-terminal addition of 15–30 amino acids, the signal or leader peptide. There is great variability as to the length and the sequence of these peptides. However, there are some general structural characteristics that must be satisfied in order for these peptides to correctly perform their function. Signal peptides have a basic amino-terminal region followed by a central hydrophobic core that may span the membrane. At the C-terminus there usually is a small uncharged amino acid.

Most of the present knowledge concerning signal peptidases (SPases) in prokaryotic systems has been derived from studies in E.coli. In this organism at least two different SPases can be distinguished. SPase I (synonymous for leader peptidase as used in this text), is capable of processing most of the proteins. A notable exception are glyceride modified lipoproteins (Tokunaga et al. 1982), which are processed by SPase II, also known as prolipoprotein signal peptidase (Tokunaga et al. 1982, Yamada et al. 1984, Yamagata et al. 1982).

The isolation and cloning of the E.coli SPase I (lep) gene is described by Date and Wickner (1981). Aliquots of cell lysates from individual colonies of a complete genomic E.coli DNA library in ColE1 plasmids were assayed for their ability to convert M13 procoat to coat protein posttranslationally. Thus, a strain could be detected that overproduced SPase I. The growth behavior of this strain (7-47) was comparable to that of other strains in the collection. Restriction fragments of pLC7-47 were recloned in pBR322. A 30-fold increase in SPase I concentration was detected in one of the strains after transformation of the plasmids into E.coli. Upon infection of this overproducing E.coli strain with M13 an increase in the transformation of procoat (precursor) to coat (integral transmembrane) protein could be detected. No effect on periplasmatic or secreted proteins was described.

The sequence of the SPase I-encoding gene (lep) from E.coli was determined by Wolfe et al. (1983), who also determined that this protein is largely found in the inner membrane.

Dalbey and Wickner (1985) have cloned and expressed the E.coli lep gene under control of the arabinose promoter and could not detect any effect on protein translocation upon expression of the lep gene. Upon repression of SPase I synthesis they found that cleavage of the signal sequence was essential for the release of the proteins from the membrane.

The effect of overproduction of the SPase I described in the above references was only determined on the M13 integral transmembrane protein. The effect on outer membrane or exported proteins was not described.

The effect of overproduction of cloned SPase I on a periplasmic (TEM beta-lactamase) and an outer membrane protein (PhoE) was reported by Anba et al. (1986). They showed that overproduction did not result in any increase in processing rates for either one of the mentioned proteins and therefore concluded that the SPase I is not the rate-limiting component with the subject precursors and under the conditions that were used.

In all of the above references the effect of SPase I overproduction on homologous proteins with their natural signal sequences was studied. Furthermore, to date the cloning and expression of the lep gene of only one species e.g. E.coli has been described.

In view of the advantages described above with respect to the use of Gram-positive bacteria in the production of recombinant proteins it could be very useful to clone and overexpress signal peptidase genes from other species then *E. coli*, particularly from Gram-positive bacteria. Although it may be expected that the homology between signal peptidase encoding genes from Gram-positive and Gram-negative bacteria may be sufficient for cross-hybridization Lampen et al. (1986) reported that they could not obtain reproducible signals upon hybridization of the *E. coli* lep gene with genomic DNA from Bacilli and *Staphylococcus aureus* in Southern blotting experiments.

As indicated above it can be expected that processing efficiency may become a rate-limiting step in the secretion of overproduced proteins. Palva (1989) suggested that it would be interesting to test whether the cloning of a signal peptidase gene or some other component of the translocation machinery would further increase production yield. However, no suggestion was made on how to perform this.

SUMMARY OF THE INVENTION

The present invention discloses for the first time a DNA sequence encoding a signal peptidase obtained from a Gram-positive bacterium. Specifically, the DNA sequence and the derived amino acid sequence of the signal peptidase of *Bacillus subtilis* are disclosed.

The present invention also shows that this sequence can be used to select the genes encoding the signal peptidase from other Gram-positive species through hybridization. It is also shown that by hybridization with DNA encoding SPaseI from a Gram-negative species (*E.coli*) the DNA encoding SPaseI can be detected in other Gram-negative species. This results in the cloning and sequencing of the SPase gene from *Salmonella typhimurium*.

The present invention further describes a method for the isolation of signal peptidase encoding genes both from Gram-positive and from Gram-negative bacteria. Said method comprises the use of specifically developed signal peptidase probe vectors. Such vectors can be used to identify a gene encoding a homologous or a heterologous signal peptidase, preferably in both Gram-negative or Gram-positive bacteria.

In another aspect expression vectors for the cloned signal peptidase are disclosed.

In yet another aspect the cloned signal peptidase encoding gene is overexpressed in a microbial host. Said host can be homologous or heterologous with the signal peptidase and it can be both a Gram-negative or Gram-positive bacterium.

In still another aspect the invention shows that co-expression of the signal peptidase gene with the gene for a periplasmic or secreted protein leads to a large increase in the processing rate of the expression product of a heterologous or homologous gene.

In a further aspect the present invention shows that some normally unprocessed gene products can be processed, by an increase in the amount of signal peptidase.

The present invention further describes a method for increasing the processing rate of some unprocessed or difficultly processed proteins by mutagenesis of the signal peptidase encoding gene. Both random and site-directed mutagenesis are described.

BRIEF DESCRIPTION OF THE DRAWINGS

FIG. 3A is a schematic representation of the *E.coli* lep operon. Relevant restriction sites are indicated (March and Inouye 1985, March et al. 1985, Wolfe et al. 1983).

FIG. 3B shows the restriction maps of the 1.3 kb *E.coli* and *S.typhimurium* PstI fragments encoding SPaseI.

Figure 7:
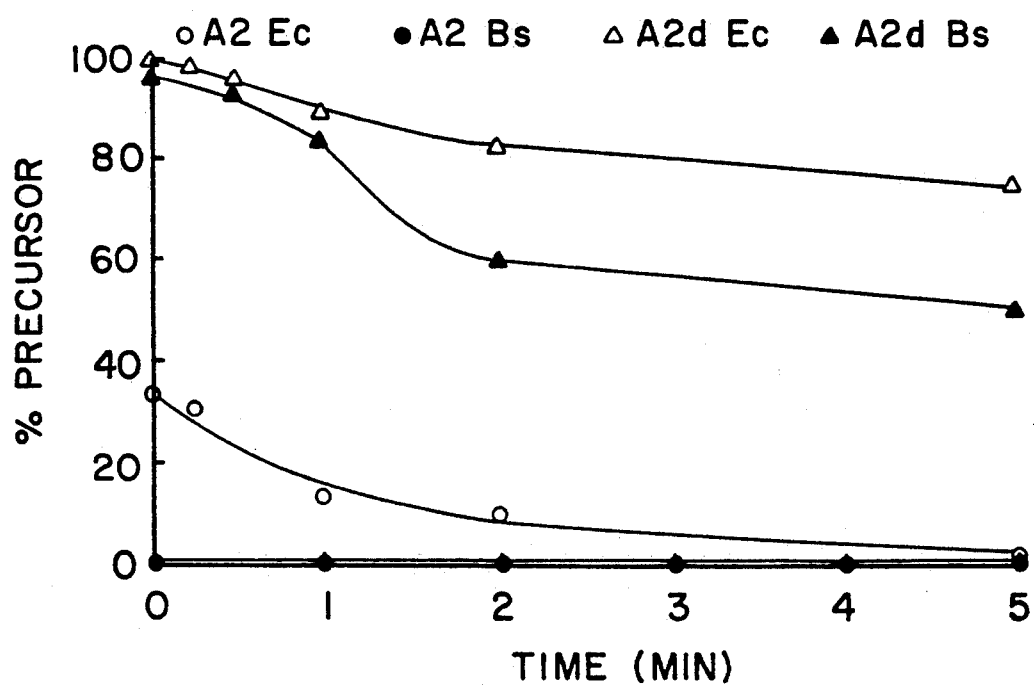
FIG. 7 shows the kinetics of processing of pre(A2)-, and pre(A2d)-α-amylase in *B. subtilis* (Bs) and *E. coli* (Eco), as determined by pulse-chase labeling. *B. subtilis* 8G5 (for α-amylases), *B. subtilis* DB114 (for β-lactamases) and *E. coli* C600 cultures containing the various plasmids were grown to log-phase at 37° C. in S7 medium and M9 medium, respectively. Cells were starved for methionine for about 30–45 min at 37° C. Proteins were labelled by incubating the cultures with [$^{35}$S]-methionine for 30 sec at the same temperature or at 25° C. in the case of pre(A2)-α-amylase and pre(A2)-β-lactamase in *B. subtilis*. Immediately after the pulse, further incorporation of radioactivity was prevented by the addition of an excess non-radioactive methionine (chase). Subsequently, samples were withdrawn at different intervals. The relative amounts of precursor and mature protein in each sample were determined by densitometric scanning of autoradiograms after immunoprecipitation and sodium dodecyl sulphate (SDS)-polyacrylamide (PAA) gel electrophoresis.

(Bs) and *E. coli* C600 (Ec). Samples were analysed by pulse-chase labeling as described (FIG. 7).

Figure 10:
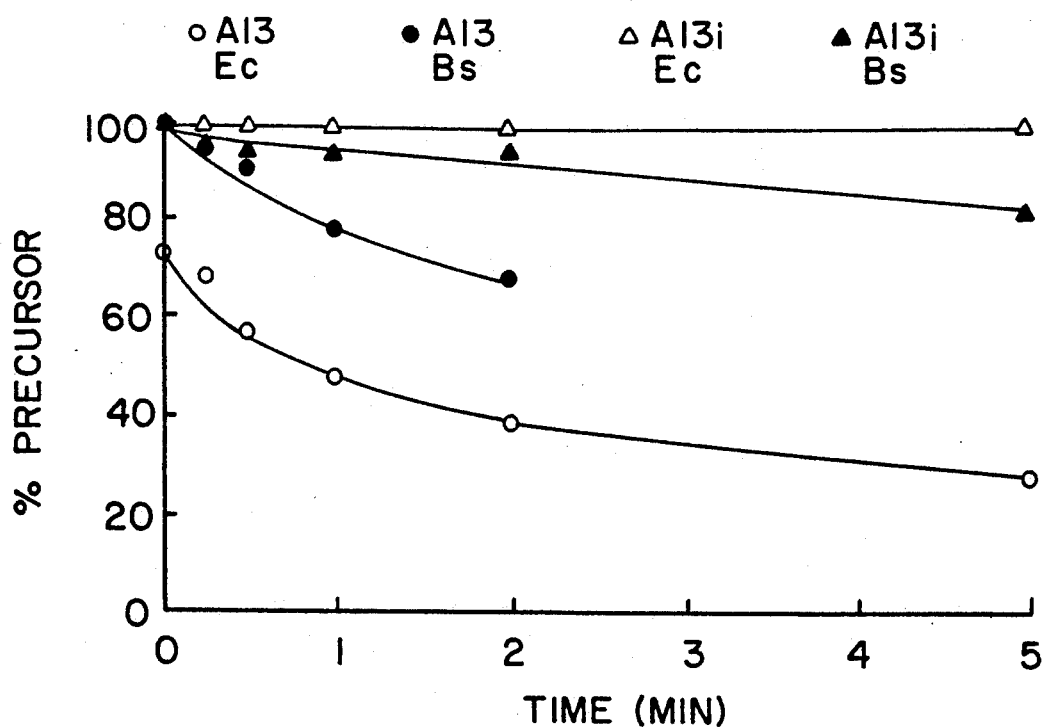

FIG. 10 shows the kinetics of processing of pre(A13)-, and pre(A13i)-β-lactamase in *B. subtilis* 8G5 or DB114 (Bs) and *E. coli* C600 (Ec). Samples were analysed by pulse-chase labeling as described (FIG. 7).

Figure 11:
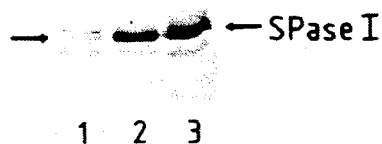

FIG. 11 shows a Western blot of SPase I. *E.coli* C600, transformed with pBS61ΔpL or pGDL2, were grown in M9 minimal medium. Exponentially growing cells were lysed in buffer containing 0.1M potassium phosphate (pH=7.2) and 0.2 mg lysozyme/ml. Similar amounts (0.02 mg total protein) were subjected to SDS-PAA gel electrophoresis. SPase I was detected with specific antisera: lane 1, *E.coli* C600(pBS61ΔpL); lane 2, *E.coli* C600(pGDL2); lane 3, reference SPase I.

Figures 12A, 12B:
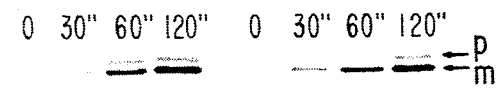
Figure 12C:
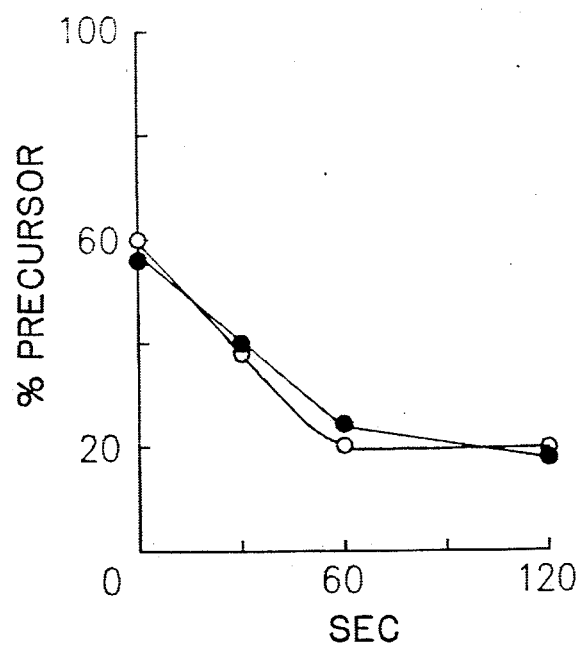

FIG. 12A and FIG. 12B show the processing of wild-type TEM-β-lactamase by *E.coli* C600(pGB25, pBS61ΔpL) and *E.coli* C600(pGB25, pGDL2), respectively. Pulse-chase labeling was performed at 25° C. and subsequent immunoprecipitation, SDS-PAA gel electrophoresis and fluorography as described in Methods. Cells were labeled for 30 s. and samples were drawn after the chase (t=0) at the indicated times. FIG. 12C shows the kinetics of processing, and is plotted as the percentage of the total β-lactamase protein (precursor+mature), that is still present in the precursor form at the time of sampling. (●) *E.coli* C600(pGB25, pBS61ΔpL); (○) *E.coli* C600(pGB25, pGDL2). p, precursor; m, mature.

FIG. 13A and FIG. 13B show the processing of pre-(A2)-β-lactamase by *E.coli* C600(pSPB-A2,pBS61ΔpL), and *E.coli* C600(pSPB-A2, pGDL2) respectively. FIG. 13C shows the analysis as described with FIG. 12C. Cells were labeled for 60 s.: (●) *E.coli* C600(pSPB-A2, pBS61ΔpL); (○) *E.coli* C600(pSPB-A2, pGDL2).

FIG. 14A and FIG. 14B show the processing of pre-(A42)-β-lactamase by *E.coli* C600(pSPB-A42, pBS61ΔpL) and *E.coli* C600(pSPB-A42, pGDL2), respectively. FIG. 14C shows the analysis as described with FIG. 10. However, labeling was performed at 37° C.: (●) *E.coli* C600(pSPB-A42, pBS61ΔpL); (○) *E.coli* C600(pSPB-A42, pGDL2).

FIG. 15A and FIG. 15B show the processing of pre-(A2d)-β-lactamase by *E.coli* C600(pSPB-A2d, pBS61ΔpL) and *E.coli* C600(pSPB-A2d, pGDL2), respectively. FIG. 15C shows the analysis as described with FIG. 11. (C): (●) *E.coli* C600(pSPB-A2d, pBS61ΔpL); (○) *E.coli* C600(pSPB-A2d, pGDL2).

FIG. 16A and FIG. 16B show the processing of pre-(A13i)-β-lactamase by *E.coli* C600(pSPB-A13i, pBS61ΔpL) and *E.coli* C600(pSPB-A13i, pGDL2), respectively. FIG. 16C shows the analysis as described with FIG. 12. (C) : (●) *E.coli* C600(pSPB-A13i, pBS61ΔpL); (○) *E.coli* C600(pSPB-A13i, pGDL2).

FIG. 17 shows an alignment of the *B. subtilis* and the *E.coli* SPAse amino acid sequences SEQ ID NO: 11 and SEQ ID No. 12.

Figure 18A:
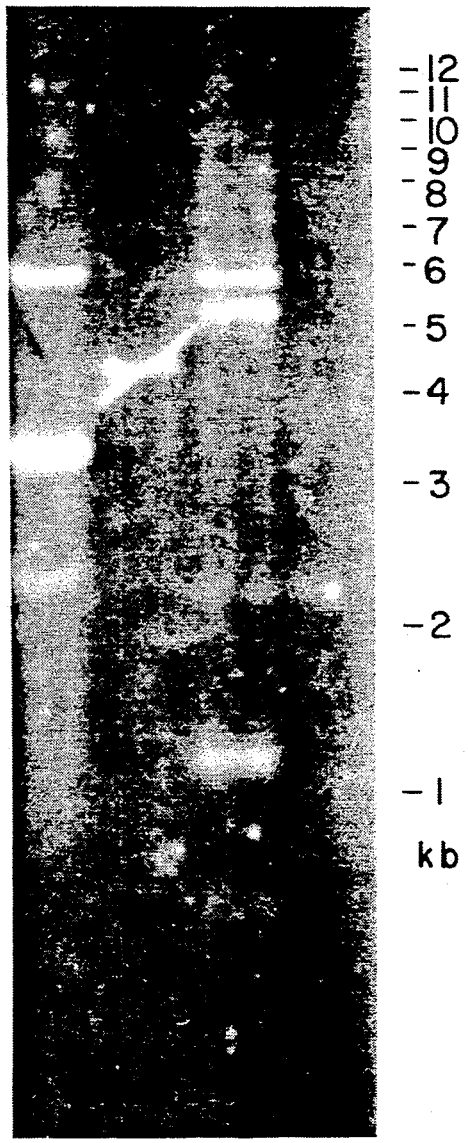
Figure 18B:
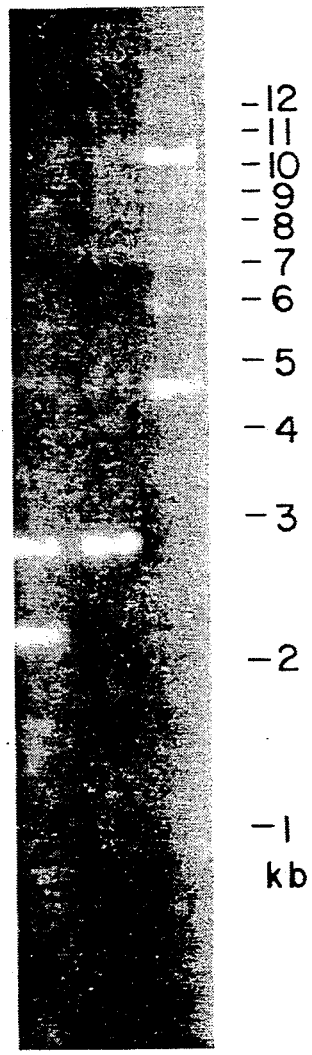

FIG. 18 shows a photograph of a Sou hybridization blotting wherein an internal fragment of the leader peptidase gene of *B. subtilis* is used as a probe. The following chromosomal DNAs have been used after digestion with; A: PstI and B: EcoRI lane 1 *Bacillus subtilis*, lane 2 *Bacillus licheniformis* lane 3 *Bacillus amyloliquefaciens*, lane 4 *Bacillus alcalophilus*.

Figure 19A:
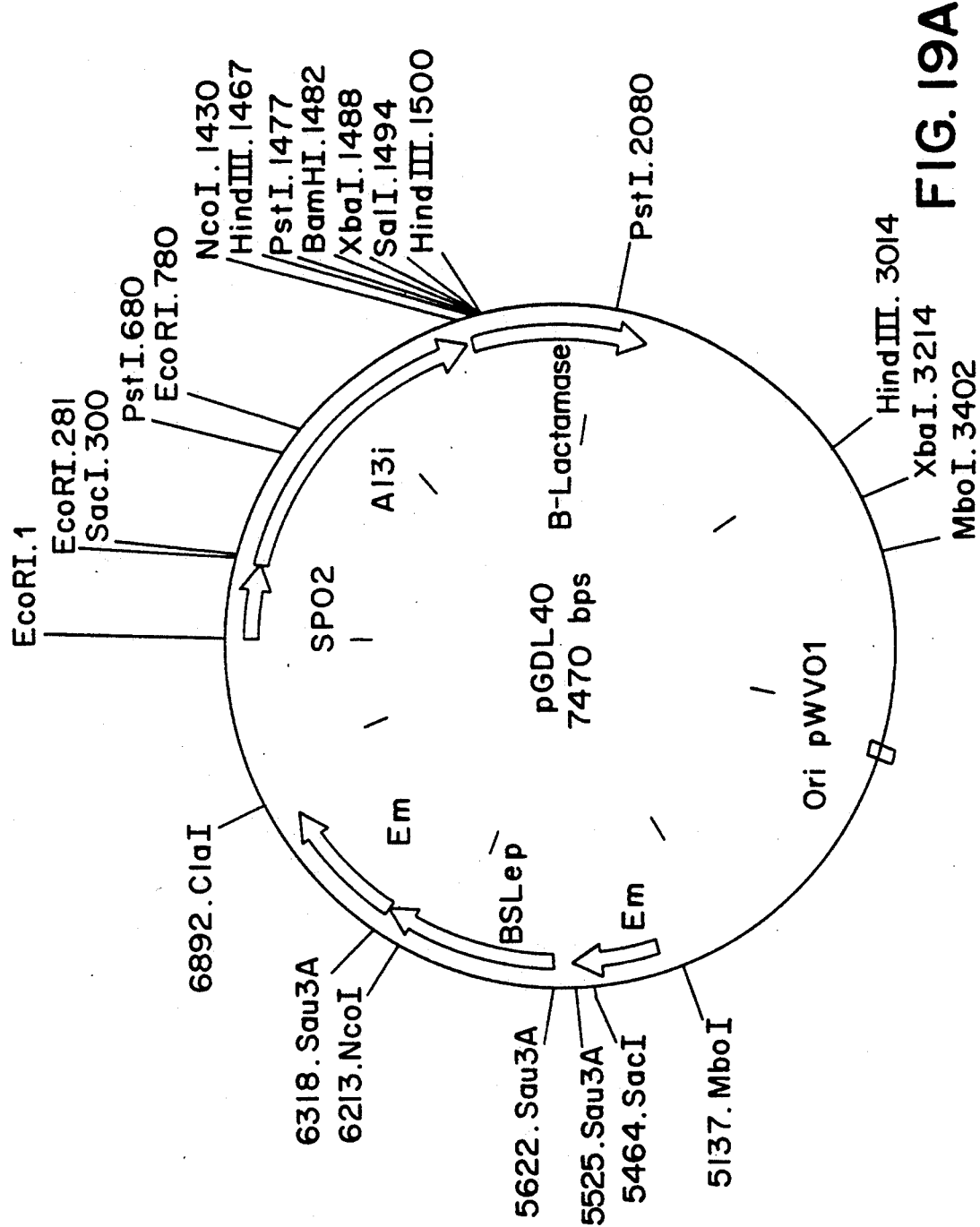
Figure 19B:
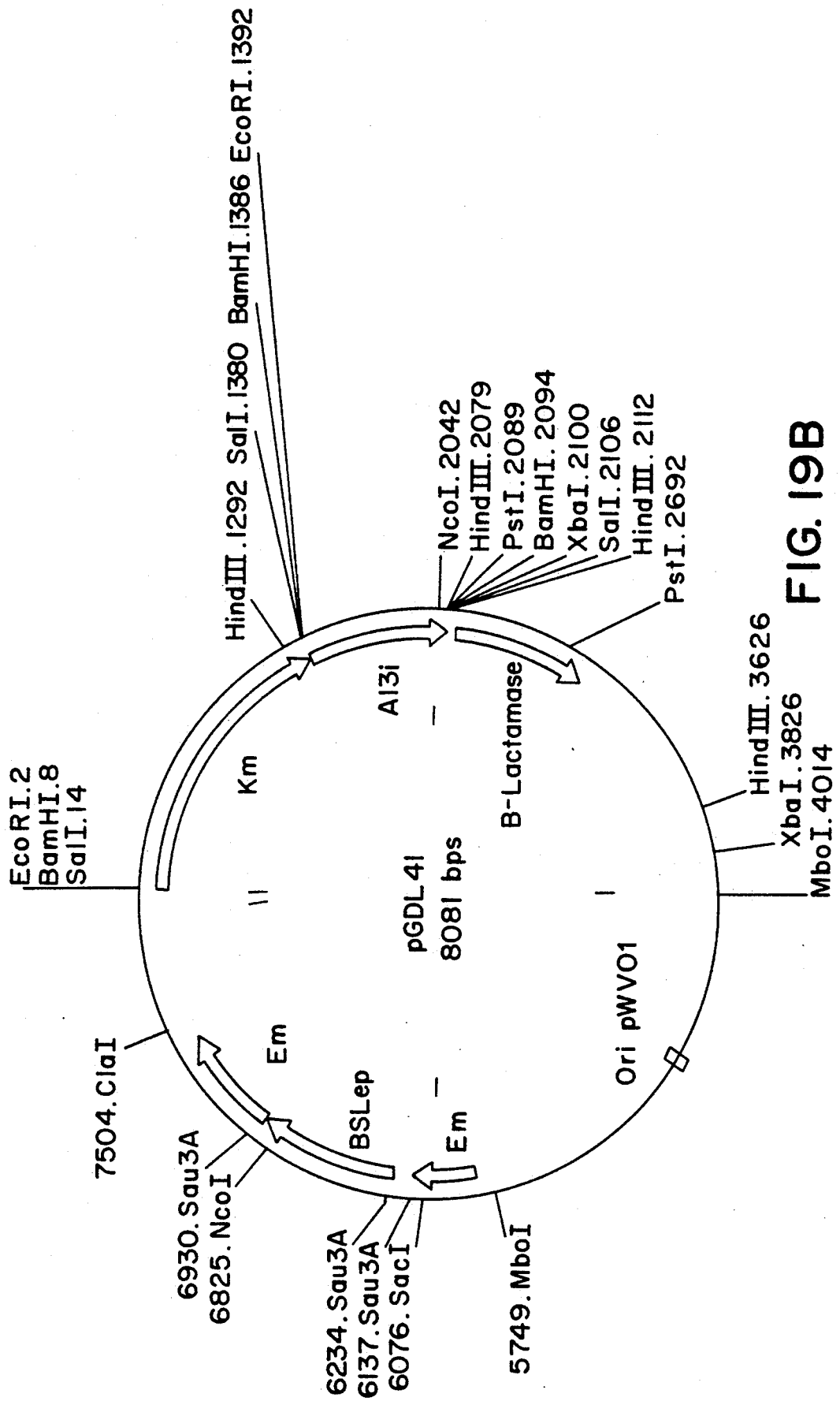
Figure 19C:
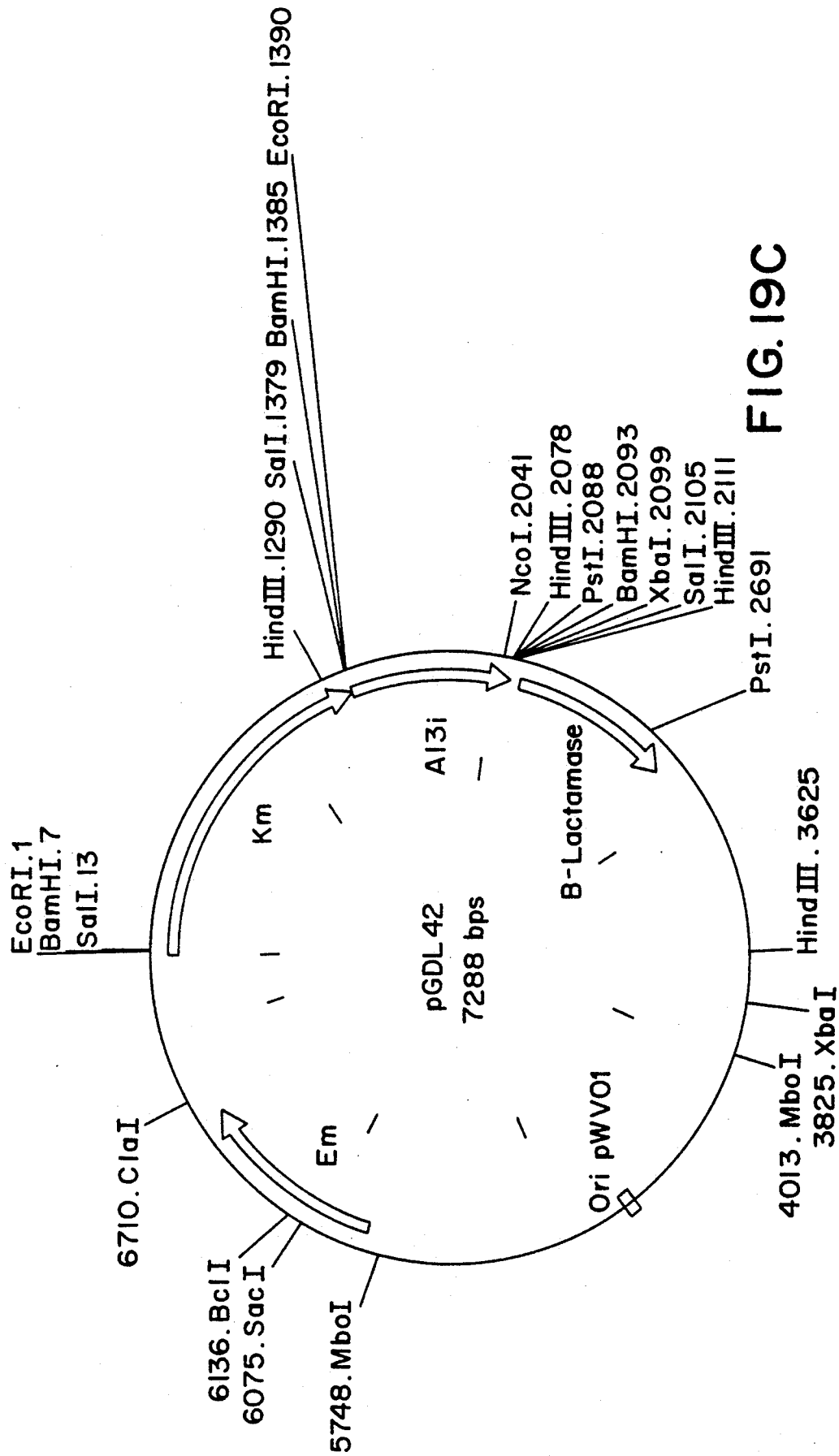

FIG. 19 shows a schematic presentation of pGDL40, pGDL41, and pGDL42. Only the restriction sites relevant for the construction and properties of the plasmids are given. Plasmid pGDL41 is a derivative of pGDL40 containing a selectable marker (Km$^r$) for *B. subtilis*. pGDL41 and pGDL42 were constructed by replacing the 0.3-kb EcoRI fragment containing the SPO2 promoter of pGDL40 and pSBA13i, respectively, by a 1.4-kb EcoRI fragment of pKM1 (Kiel et al., 1987) containing a *Streptococcus faecalis* Km$^r$ gene.

FIG. 20 pulse-chase analysis of pre(A13i)-β-lactamase processing. The processing of pre(A13i)-β-lactamase by *B. subtilis* DB104(pGDL41) (A, B, and E) and *B.subtilis* DB104(pGDL42) (B, D, and E) was analysed by pulse-chase labeling at 37° C. and subsequent immunoprecipitation, SDS-PAA gel electrophoresis and fluorography. A and B: cells from four separate cultures of *B. subtilis* DB104(pGDL41) (lanes 1-4) and *B.subtilis* DB104(pGDL42) (lanes 5-8), respectively, were labeled for 1 min and samples were drawn immediately after the chase (t=0). C and D: Cells of *B. subtilis* DB104(pGDL41) (C) and *B.subtilis* DB104(pGDL42) (D) were labeled for 1 min and samples were drawn at the indicated times. The kinetics of processing are plotted as the percentage of the total (A13i)-β-lactamase protein (precursor plus mature), which is still present in the precursor from at the time of sampling. E: (○) *B. subtilis* DB104(pGDL41); (●) *B.subtilis* DB104(pGDL42). p, precursor; m, mature.

FIG. 21 shows an alignment of the amino acid sequences of *B. subtilis*. *E. coli* and *Salmonella typhimurium* SPase I, the SEC11 protein of *Saccharomyces cerevisiae* and the canine 21K protein SEQ ID NO:13, SEQ ID NO:14, SEQ ID NO:15, SEQ ID NO:16 and SEQ ID NO:17. The conserved Asp and Ser are indicated (*).

DETAILED DESCRIPTION OF THE INVENTION

Most of the proteins that are secreted by microorganisms are preceded by a hydrophobic sequence that facilitates the integration of the protein into the cellular membrane. In eukaryotes similar sequences are found for transporting proteins over the endoplasmatic reticulum membrane. These sequences are called signal peptides. The integration of these signal peptides into the membrane is a prerequisite for the export of these proteins. Due to their hydrophobic nature the signal peptides stay in the membrane as a kind of anchor. The protein 'pulled' through the membrane, but it stays anchored in the membrane due to the signal peptide. To release the protein into the medium (or periplasm) a proteolytic enzyme is needed to cleave the protein immediately after the signal peptide. These proteolytic enzymes are the signal peptidases. Signal peptidases form the subject of the present invention.

DNA encoding a signal peptidase can in principle be isolated from all microorganisms that are capable of secreting proteins, via the described mechanism involving a signal peptide. The methods described in this invention can be used with both Gram-positive and Gram-negative bacteria as DNA donors. Preferably, Gram-positive microorganisms are used. More preferably Bacilli are used.

Different approaches for the isolation of a gene encoding a signal peptidase can be used. In a preferred embodiment a the DNA of a host organism is recombined in such a way that the chromosomal signal peptidase gene is brought under control of a regulatable promoter. Different regulatable promoters can be used. For example a sugar inducible or a temperature sensitive promoter. In one of the preferred embodiments of the present invention the phage lambda $P_L$ promoter is used. The promoter of choice is cloned on a vector containing one or more sequences that are homologous with sequences surrounding the chromosomal signal peptidase gene, such that this vector can integrate. Integration is performed, for example through homologous recombination, in such a way that ultimately the inducible promoter becomes operably linked with the signal peptidase gene. In the repressed state the strain is unable to grow, but growth is restored if a functional leader peptidase gene is introduced. The introduction of the lep gene can be performed with a leader peptidase probe vector. One such a vector pGD40 has specifically been constructed.

After cloning of random DNA fragments from a donor microorganism in a signal peptidase probe vector and subsequent transformation of the mutated host microorganism some clones are found to have restored protein processing activity and growth inhibition is suppressed. Said clones will contain an active leader peptidase gene that complements the mutated host organism gene (Van Dijl et al. 1988 and 1990).

The described method for selecting a signal peptidase gene can be used in every combination of host and gene provided that the cloned signal peptidase gene is active in the host organism used. The invention is exemplified by E.coli as a host and S.typhimurium as a DNA donor species. Other preferred donors, also exemplified herein, are Bacilli.

In another preferred embodiment a reporter gene is cloned behind a DNA sequence encoding a signal peptide which greatly reduces the export efficiency of the reporter gene encoded protein. This construct is inserted into an expression vector and the vector is brought into a host cell. The vector can be self-replicating or it can be integrating. The reporter gene can be any gene for which an assay is available or can be developed. A suitable assay is available for α-amylase. In the present invention a halo assay for β-lactamase is developed. As signal peptides; A2, A13 and A42 (as described in EP 244042) and derivatives thereof A2d, A13i and A42d are used. These signal sequences have originally been randomly selected from the Bacillus subtilis chromosome on the basis of their favourable export characteristics. The derivatives contain either a deletion (d) or an insertion (i) which greatly influences their processing characteristics in E.coli and/or in B. subtilis. Using these and similar constructs not only allows the detection of cloned signal peptidases but also allows for a detailed study of the effects of overexpression of cloned lep genes in different host species.

Subsequently a genomic library is made. Host cells are transformed with expression vectors, each containing a fragment of genomic DNA. The reporter gene may be cloned on a different or on the same vector. A clone showing halo formation in a plate assay will contain an active lep gene since the SPase that is produced will restore the processing efficiency of the reporter protein. Otherwise a halo would not be formed. Provided that the export deficiency of the reporter protein is at the SPase I level. It will be clear to a person skilled in the art that the described or similar vectors can also be (and are also at the same time) used to obtain other DNA elements that encode a limiting factor for protein processing activity. In this respect one can think of for example, proteins which are functionally equivalent to E.coli secA, secB, secY, secD, secF and secE (Bieker and Silhavy, 1990).

This method is used in the present invention to obtain the signal peptidase gene of a Gram-positive bacterium. Exemplified herein is the cloning of the signal peptidase gene from B. subtilis.

Another way of obtaining a signal peptidase gene is also possible. A signal peptidase (protein) can be isolated and N-terminally sequenced. From this sequence the degenerate base sequence can be deduced. A probe can be synthesized against this sequence and used to detect a clone in a DNA library containing the genome of the corresponding microorganism. The sequence can be determined and the DNA cloned in an expression vector.

It is also possible to obtain a lep gene by using a known lep gene as a probe. For example, the SPase I and the SPase II genes of E. coli have been cloned and are thus available as probes. In the present invention the a BglII-EcoRI 931-bp fragment carrying part of the 3' end of the lepA and the 5' end of the lep gene from E.coli obtained from pTD142 was used as a probe to detect the S. typhimurium lep gene. The lep gene was detected, sequenced and overexpressed. This shows the feasibility of the use of hybridization to obtain the lep gene of other microorganisms. In a similar way probes derived from the B. subtilis lepBS gene were used to detect the DNA encoding the lep gene from other Gram-positive bacteria.

The cloning of the signal peptidase DNA can be performed using an expression vector of choice (plasmid, cosmid, bacteriophage, virus). Positive clones will be those having restored growth. From these clones it is possible to isolate and characterize the gene. The gene can be isolated and recloned into a suitable host. Suitable hosts are all hosts in which the cloned SPases are functional. These host can be homologous or heterologous with the lep gene. Examples of suitable hosts useful in practicing the present invention are Salmonella. E.coli and Bacilli. It is obvious that in principle every host that is compatible with the cloned lep gene can be used.

The vector containing the cloned gene can be brought into the cell, for example by transformation. It is possible to use a self-replicable vector. It is also possible to integrate the vector into the genome.

The cloned signal peptidase gene can be overexpressed which leads to an increase in the processing rate of those signal peptide containing proteins which have a limitation in their processing rate at the level of the signal peptidase. Said proteins may be constitutively expressed in the host. It is also possible to clone heterologous proteins in the host organism. These heterologous proteins can be inserted in the genome or in a suitable cloning vehicle. Limitations in the processing rate may be found for example when;

a) the amount of signal peptidase becomes limiting. This can occur when homologous or heterologous proteins are overexpressed, especially when high level production is concerned.

b) the amino acid sequence around the signal peptide splice-site is non-optimal. This depends on the combination of protein signal-peptide and signal peptidase (host organism).

In such cases the overexpression of the co-expressed SPase gene can sometimes overcome this rate-limitation. Preferably the host organisms are Gram-positive bacteria, although Gram-negative bacteria are not excluded.

Another problem that can partly be avoided by overexpression of SPase is the incompatibility of the SPase processing site of the heterologous or partly heterologous expression product with the host SPase. Overexpression of the SPase of the host organism may be used to increase the processing rate of the foreign protein. Alternatively, overexpression of a heterologous SPase may be used. In the mentioned case it can also be useful to co-express the SPase gene in the organism where the heterologous gene comes from. It will be clear that overexpression of any DNA fragment encoding a factor limiting to protein translocation can help to improve secretion of proteins.

Compatibility of the processing site with the cloned signal peptidases can further be increased by site-directed mutagenesis or random in vitro mutagenesis on the cloned peptidase gene. Upon comparison of the sequences of signal peptidases obtained from different microorganisms conserved regions emerge. Conserved amino acids are generally involved in the reaction catalyzed by the enzyme. Therefore differences in or around (in a spatial way) these active site amino acids are involved in the specificity of the enzyme. Differences found between E.coli, B. subtilis, and S. typhimurium suggest some possible site-directed mutations. A selection assay based on the A2-α-amylase, the A2-β-lactamase, the A13-α-amylase or the A13-β-lactamase precursor cleavage (Smith et al., 1988) can be used to select those mutant lep genes, that can cleave the subject processing site.

In a preferred application of the present invention the signal peptidase is cloned and overexpressed in a host containing a gene that encodes a protein of choice and that is overexpressed. If the processing of the protein of choice is limited the signal peptidase is mutagenized through random mutagenesis using for example "spiked" oligo mutagenesis (Hermes 1989) and the strain having an increased processing rate is selected. Thus one arrives at an optimal combination of expression construct and signal peptidase.

The enzymes of the present invention are specific for removing the signal peptides from polypeptides. Although the examples demonstrate the invention with signal peptidase I from E.coli, S.typhimurium and Bacillus, it will be apparent that other microorganisms may also be used as a source for isolating or as a host for overexpressing the signal peptidase gene.

Although the present description contains all the information for practicing the invention the lepBS gene in pGDL40 has been deposited in a E.coli WK 6 at the CBS in Baarn, the Netherlands. On Feb. 19, 1991 under no CBS 116.91.

EXPERIMENTAL

Media and Plates

TY medium contained (per liter) Bacto tryptone (1%), Bacto yeast extract (0.5%) and NaCl (1%). M9 medium (Miller 1972) for E. coli contained glucose (0.4%), CaCl$_2$ (15 μg/ml), MgSO$_4$.7H$_2$O (250 μg/ml), casamino acids (0.02%), thiamine (1 μg/ml) and thymidine (2 μg/ml). M9 medium-2 is a methionine- and cysteine-free medium which differed from M9 medium-1 in that the MgSO$_4$.7H$_2$O was replaced by MgCl$_2$ (250 μg/ml) and the casamino acids by a solution of all amino acids (250 μg/ml) except methionine and cysteine. If required, erythromycin (100 μg/ml) and kanamycin (20 μg/ml) were added. S7 medium used in the pulse-chase labeling of B. subtilis DB114(pGDL41, pGDL42) was basically according to Vasantha and Freese (1980) with the modification that 3-(N-morpholino)propanesulfonic acid was replaced by 20 mM potassium phosphate (S7 medium-1). S7 medium-3 was a methionine-free variant of S7 medium-1. Both media were supplemented with kanamycin (10 μg/ml).

DNA Techniques

Procedures for DNA purification, restriction, ligation, agarose gel electrophoresis, and transformation of competent E. coli cells were carried out as described by Maniatis et al. (1982 or 1989, 2nd ed.) or Ausubel et al. (1987). Enzymes were from Boehringer (Mannheim, FRG).

Pulse-Chase Labeling

E.coli: Pulse-chase labeling of proteins to study the kinetics of processing in E. coli was carried out essentially as described by Minsky et al. (1986). Exponentially growing cells in M9 medium-1, supplemented with 0.2 mM isopropyl-β-D-thiogalactopyranoside (IPTG), were washed once with M9 medium-2 and incubated for 45 minutes in this methionine- and cysteine-free medium, which was also supplemented with IPTG. Labeling with [$^{35}$S]-methionine (50 μCi/μl; 1330 Ci/mMol; Radiochemical Centre, Amersham, UK), chase with excess (2.5 mg/ml) non-radioactive methionine and cysteine, and sampling, followed by immediate precipitation with trichloroacetic acid (TCA, 0° C.), were performed as described previously (Van Dijl et al. 1988).

B. subtilis: Exponentially growing cells in S7 medium-1 were washed once with the methionine-free S7 medium-3, and incubated for 45 minutes at 37° C. in this medium. Labeling with [$^{35}$S]-methionine (40 μCi/ml; 1330 Ci/mMol; Radiochemical Center, Amersham, UK) for the times indicated, chase with excess (2.5 mg/ml) non-radioactive methionine, and sampling followed by the immediate precipitation of proteins with trichloroacetic acid (TCA; 0° C.), were performed as described previously (van Dijl et al., 1988). Precipitates were resuspended in 100 μl of 10 mM Tris-hydrochloride (pH 8.0); 25 mM MgCl$_2$; 200 mM NaCl and 5 mg/ml lysozyme (Boehringer, Mannheim, FRG). After 10 min at 37° C. lysis was completed by the addition of 10 μl 10% sodium dodecyl sulphate (SDS) and heating for 10 min at 70° C.

Spheroplasting

To study the localisation of precursors and mature enzymes pulse-chase labeling experiments were performed as described above. However, samples were not immediately precipitated with TCA, but incubated for 30 minutes with spheroplast buffer (100 mM Tris.HCl (pH 8.0) 0.5M sucrose, 10 mM EDTA, 0.1 mg/ml lysozyme, 0° C.). Spheroplasts and periplasmic contents were then separated by centrifugation prior to precipitation with TCA.

Immunoprecipitation, PAA Gel Electrophoresis and Fluorography

Immunoprecipitation was carried out as described by Edens et al. (1982) with specific antisera. Sodium dodecyl sulfate (SDS)-polyacrylamide (PAA) gel electrophoresis was performed according to the method of Laemmli (1970). [$^{14}$C] methylated molecular weight reference markers were from Amersham (Radiochemical Centre, Amersham, UK). Fluorography was performed as described by Skinner and Griswold (1983). Relative amounts of radioactivity (pulse-chase), or alkaline phosphatase staining (Western blotting) were estimated by densitometer scanning with an LKB ultroscan XL enhanced laser densitometer (LKB, Sweden).

Western Blot Analysis

The expression of SPase I was immunologically characterized by Western blotting (Towbin et al. 1979). After SDS-PAGE, proteins were transferred to nitrocellulose membranes (BA 85; Schleicher and Schuell, Dassel, FRG) by electroblotting. SPase I production was then monitored by incubating the membranes with specific antibodies, and subsequent tracing of bound antibodies with alkaline phosphatase (AP)-antirabbit IgG conjugates (ProtoblotR, Western Blot AP system, Promega Biotec). SPase I, which was used as a marker, was purified from an overproducing strain as described by Wolfe et al. (1983).

In Vitro Transcription, Translation and Processing

[$^{35}$S]-labeled precursors of exported proteins were synthesized in vitro and their processing by purified SPase I at 37° C. was studied as described by de Vrije et al. (1987). In the co- and post-translational processing assays SPase I was added to the translation mixture 5 min and 25 min after the start of the translation, respectively. Incubation with SPase I was continued for 30 min.

Assay for β-Lactamase Activity and Processing on Plates

β-Lactamase activity was assayed essentially as described by Chevallier and Aigle (1979). The assay is based on the ability of penicillinases to catalyse the hydrolysis of penicillin to penicilloic acid, which in turn is able to reduce a blue-coloured starch-iodine complex, resulting in decoloration. Transformed E. coli MC1061 cells were plated onto TY medium containing agar (2%), starch (0.2%; Janssen Chimica, Beerse, Belgium), 50 mM potassium phosphate buffer (pH 6.5) and ampicillin (40 μg/ml). After overnight incubation at 37° C., 6.5 ml of a deep blue soft (TY) agar assay medium, containing agar (1.3%), starch (0.13%), iodine reagent (0.23% I2+1% KI), ampicillin (1 mg/ml), and 40 mM potassium phosphate buffer (pH 6.5), was poured on the plates with transformants. After the overlayer had become solid, the plates were incubated for approximately 15 min. at 30° C. White halos appeared around colonies that produced β-lactamase and released the mature protein into the periplasm.

EXAMPLE I

Construction of the Signal Peptidase Probe Vector pGD40

Figure 1:
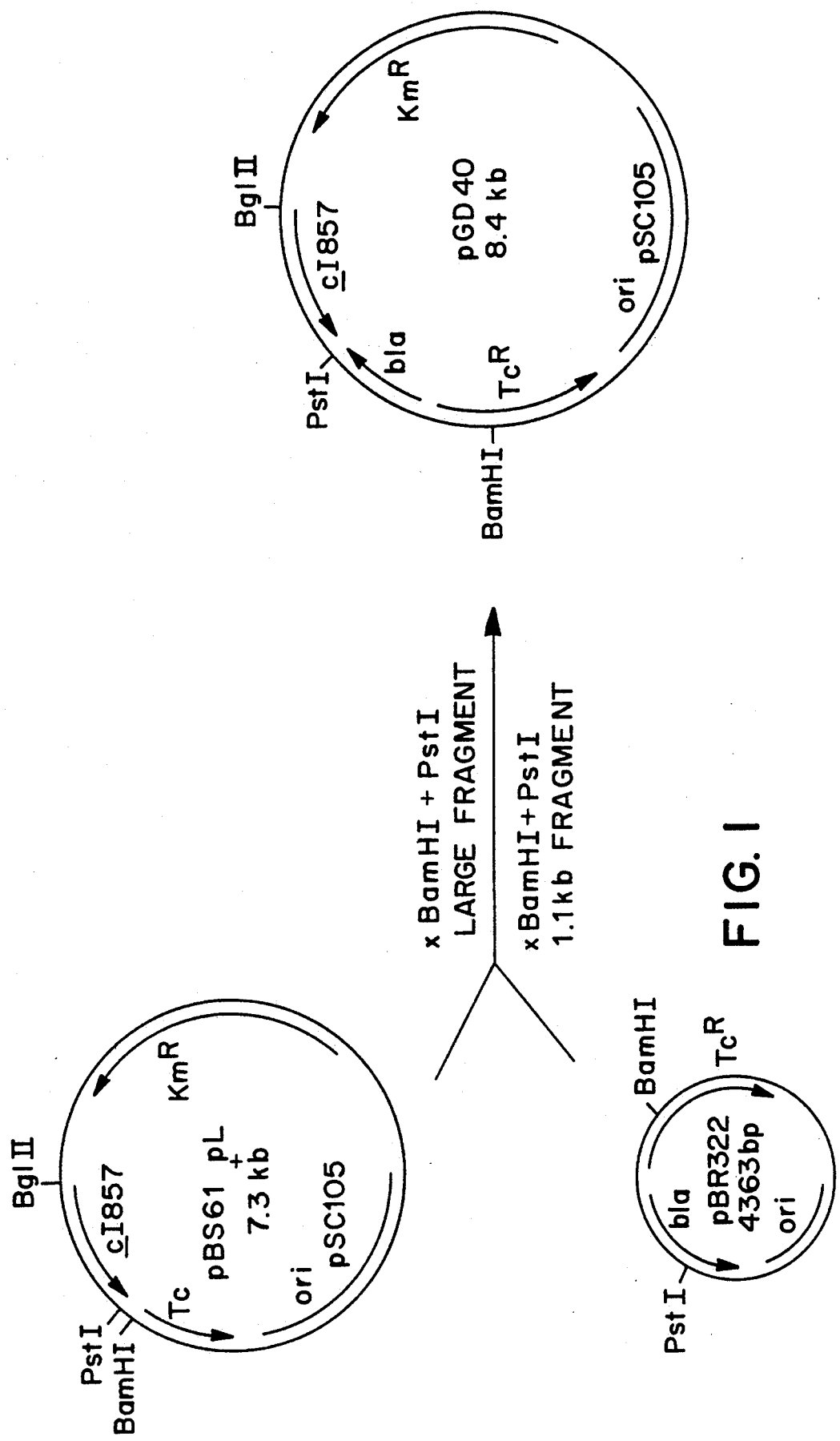
FIG. 1 shows the construction of pGD40. Relevant restriction sites are indicated. pGD40 was constructed by replacing the 44 bp PstI-BamHI fragment from pBS61 pL by a 1.1 kb PstI-BamHI fragment from pBR322. Tc' and bla' represent a 5' deletion of the tetracyclin resistance gene and a 3' deletion of the β-lactamase gene, respectively. The tetracyclin resistance gene is restored in pGD40.

In E.coli N4156::pGD28, the lep gene is transcribed from the repressible phage lambda P$_L$ promoter (van Dijl et al. 1988). In the repressed state, the strain is unable to grow, but growth is expected to be restored if a functional lep gene, encoding SPase I activity is introduced. To that purpose plasmid pGD40, carrying two antibiotic resistance markers (Km$^r$ and Tc$^r$) and the phage lambda cI857 gene, encoding temperature-sensitive repressor, was constructed (FIG. 1). The presence of this repressor renders transcription of lep in E.coli N4156::pGD28 controllable. Due to the strategy chosen for its construction, pGD40 also encodes a C-terminally truncated, enzymatically inactive β-lactamase. Recombinants of this plasmid can be selected by cloning into the unique BamHI site, and selection for tetracyclin-sensitive transformants. In addition, depending on the orientation of the cloned fragments, transcription of foreign genes, even if they might lack their own promoters, would be possible under the control of the promoter of the tetracyclin resistance gene (pTc$^r$).

EXAMPLE II

Complementation Assay With the Homologous E.coli Lep Gene Cloned in pGD40

Figure 2:
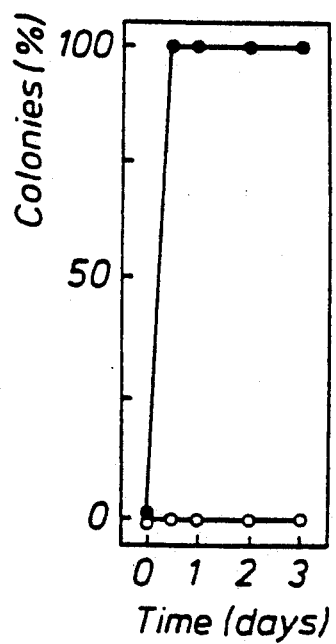
FIG. 2 shows growth of transformed *E.coli* N4156::pGD28 at 28° C. The viability of 50 transformants of each class, obtained at 28° C., was tested by transfer to fresh plates and incubation at 28° C. The percentage of toothpickings on fresh plates that developed into colonies was determined as a function of the time of incubation. (○):pGD40; (●): pGDL05 or pGDL06.

A 2.3 kb pTD142 derived BamHI-BglII fragment, containing the promoterless E.coli lep gene (Date and Wickner 1981, Wolfe et al. 1983), was cloned into the BamHI site of pGD40. This resulted in pGD105 carrying the lep gene under the transcriptional control of pTc$^r$, and in pGDL06 carrying the lep gene in the opposite orientation. The viability of E.coli N4156::pGD28 after transformation with pGD40, pGDL05 and pGDL06 was tested at 28° C. and 42° C., that is under repressed and derepressed conditions, respectively. At 42° C., when the chromosomally located lep gene is expressed, transformants carrying pGD40, pGDL05 or pGDL06 showed wild-type growth properties. In contrast, at 28° C., when the chromosomal lep gene is repressed, transformants carrying pGD40 had lost their colony-forming capacity when transferred by toothpicking to fresh plates, whereas transformants carrying either pGDL05 or pGDL06 did form colonies (FIG. 2). Notwithstanding the wrong orientation of the lep gene in pGDL06 with respect to pTc$^r$, the transformants harbouring this plasmid produced sufficient SPase I to prevent cell death, although growth at 28° C. was clearly impeded.

EXAMPLE III

Figure 4:
FIG. 4 Southern hybridization of a [$^{32}$P]-labeled 931 bp BglII-EcoRI fragment of the *E.coli* lep operon with PstI cleaved chromosomal DNA of *S.typhimurium* (lane 1). Lane 2 and 3 show the hybridization of the same probe with PstI cleaved pUC9 carrying the selected 1.3 and 1.0 kb *S.typhimurium* DNA fragments, respectively.

Molecular Cloning of S.typhimurium DNA Fragments Homologous With the E.coli Lep Operon and Identification of the S.typhimurium Lep Gene Chromosomal S.typhimurium DNA, digested with various restriction enzymes, was analysed by Southern blotting using a 931-bp pTD142 derived BolII-EcoRI fragment, carrying the 3' end of the lepA-gene (249 bp) and the 5' end of the lep gene (664 bp) (March and Inouye 1985, Wolfe et al. 1983), as a hybridization probe (FIG. 3A). Two hybridizing S. typhimurium PstI DNA fragments, of 1.0 kb (weak signal) and 1.3 kb (strong signal), respectively, could be identified (FIG. 4, lane 1). To clone these fragments, size fractionated (0.9–1.4 kb), PstI-cleaved chromosomal DNA, extracted from agarose gels, was ligated into PstI-cleaved pUC9. E.coli JM83 was transformed with the ligation mixture and white ampicillin-resistant transformants carrying the 1.0 or 1.3 kb fragment were selected by colony hybridization using the 931-bp BglII-EcoRI E.coli lepA-lep fragment as a probe (FIG. 4, lane 2 and 3). Both fragments were subcloned in the PstI site of pUC7 and excised from this plasmid by BamHI. These fragments were subsequently inserted in two orientations into the unique BamHI site of the Tc$^r$ gene in pGD40. This resulted in pGDL11 and pGDL12 (carrying the 1.3 kb fragment in both orientations), and in pGDL13 and pGDL14 (carrying the 1.0 kb fragment in both orientations). pGDL11, pGDL12, pGDL13 and pGDL14 were used to transform E.coli N4136::pGD28, and growth and viability properties at 28° C. of the transformants were examined. Transformant-colonies of N4156::pGD28(pGDL13 or pGDL14) were markedly smaller than those of N4156::pGD28(pGDL11 or pGDL12), indicating a difference in growth rate depending on the nature of the fragment inserted in pGD40. Transfer by toothpicking to fresh plates revealed that transformants harbouring pGDL13 or pGDL14, like transformants harbouring pGD40, had lost their colony forming capacity at 28° C. In contrast, transformants harbouring pGDL11 or pGDL12, like transformants harbouring pGDL05 or pGDL06, showed no impaired viability. Furthermore, the viability of all transformants was unaffected at 42° C. (data not shown). These data strongly suggest that the 1.3-kb S.typhimurium PstI fragment encoded a lep gene which complemented inhibited E.coli SPase I synthesis. E. coli N4156::pGD28(pGDL11) showed a higher growth rate at 28° C. than N4156::pGD28(pGDL12), whereas their growth rates at 42° C. did not differ. This observation suggests that the expression of S.typhimurium SPase I in pGDL11 is controlled by pTc$^r$. Restriction enzyme analysis of the 1.3 kb S.typhimurium PstI fragment revealed that the restriction map of the S.typhimurium fragment differed considerably from that of the corresponding 1.3 kb PstI fragment carrying the E. coli lep gene (FIG. 3B).

EXAMPLE IV

Sequencing and Further Identification of the S.typhimurium Lep Gene

To determine the nucleotide sequence of the S.typhimurium lep gene, the 1.3 kb PstI fragment was sequenced (see Sequence Listing; SEQ ID NO:3 and SEQ ID NO:4). SEQ ID NO 3 and SEQ ID NO:4 shows the nucleotide sequence and the deduced amino acid sequence of the S.typhimurium lep gene (bases 125 to 1099) and flanking regions. Nucleotide numbering starts with the PstI site. The amino acids that are different or lacking (---) in the E.coli SPase I amino acid sequence, are indicated. The Shine-Dalgarno sequence of the lep gene is underlined (positions 113–119). Stop codons are indicated (End). The arrows downstream of the lep gene mark the terminator-like inverted repeat. The -35 and -10 regions downstream of this inverted repeat represent the putative rnc promoter (March et al. 1985).

Comparison of the S. typhimurium nucleotide sequence with the sequence of the corresponding 1.3 kb E.coli PstI fragment (March et al. 1985, March and Inouye 1985, Wolfe et al. 1983), revealed a high degree of over-all sequence similarity (83% matches/length). Like the E.coli fragment, the S.typhimurium fragment contained two open reading frames (SEQ ID NO:3 and SEQ ID SO:4), one of which (bases 1–108) shares sequence similarity with the 3' end of the E.coli lepA gene (108 bp with 95.4% matches/length) and the other (bases 125–1099) with the E.coli lep gene (975 bp with 83.5% matches/length). The deduced amino acid sequence of the carboxyl-terminal end of the S.typhimurium lepA protein appeared to be identical to that of the E.coli lepA protein, whereas the deduced amino acid sequence of the S.typhimurium SPase I compared to that of the E.coli SPase I showed 23 mismatches and 1 additional amino acid (92,5=6% match/length). The calculated Mw of the S.typhimurium SPase I (consisting of 324 amino acids) is 35,782.

Figure 5:
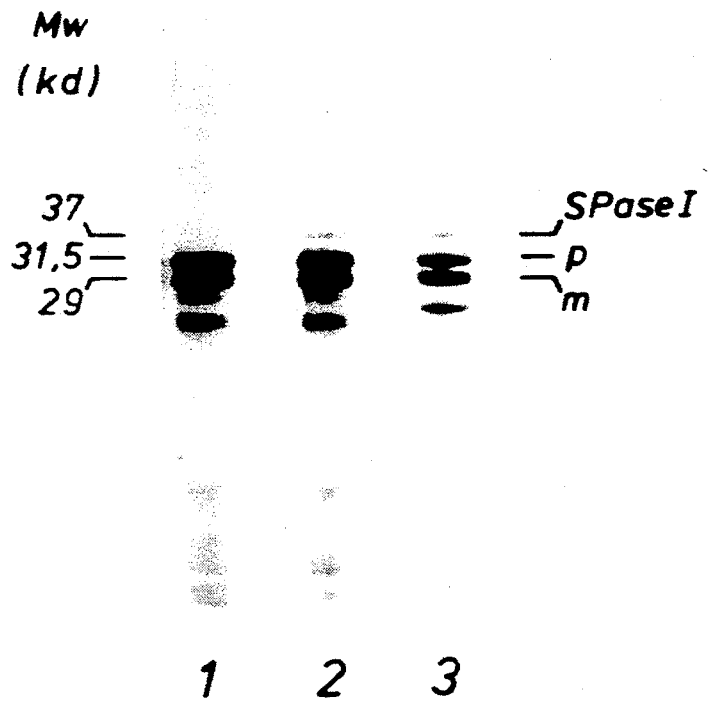
FIG. 5 shows the in vitro transcription/translation products directed by pUC9 (lane 1), pUC9 carrying the 1.3 kb PstI fragment from *S.typhimurium* (lane 2) and pTD142 (lane 3). P and M indicate the positions of pre-β-lactamase and the mature enzyme, respectively.

In vitro translation of pUC9, carrying the 1.3 kb PstI fragment, showed that it encoded a protein with an apparent molecular weight of 36,000 dalton, which comigrated with the E.coli SPase I on SDS-PAGE (FIG. 5). This is in good agreement with the calculated Mw of 35,782 for the S.typhimurium lep gene and 35,994 for the E.coli lep gene.

EXAMPLE V

Processing of TEM-$\beta$-Lactamase in E.coli N4156::pGD28

Figure 6:
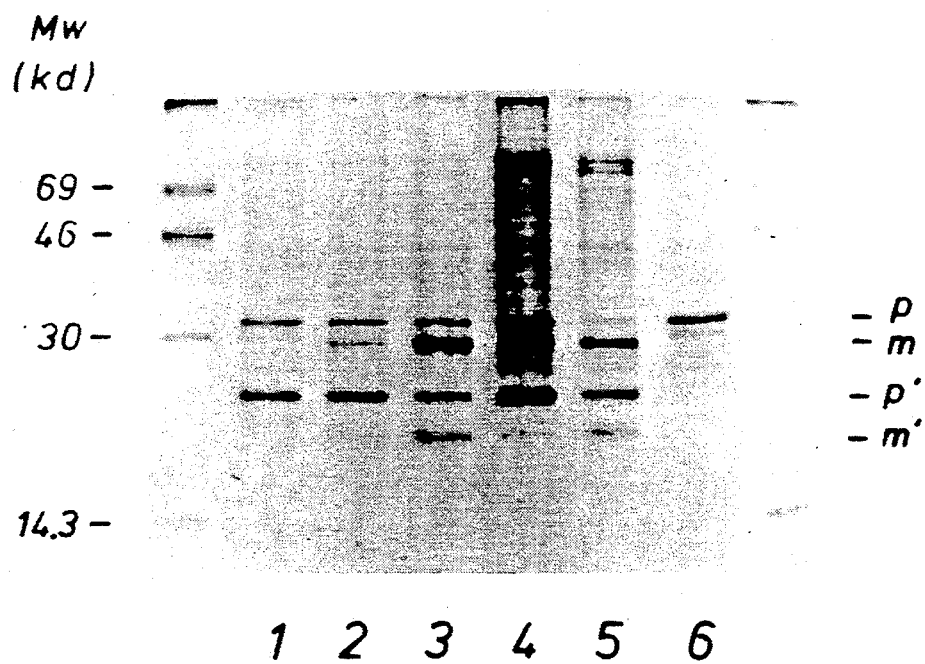
FIG. 6 shows the processing of *E.coli* TEM-β-lactamase. Preparation of cultures, pulse-chase labeling and the analysis of samples taken 15 s after the chase were as described in Experimental. The processing products indicated are from pGD40 (lane 1), pGDL06 (lane 2), pGDL05 (lane 3), pGDL12 (lane 4), pGDL11 (lane 5), pGDA2 (lane 6). P and M indicate the positions of pre-β-lactamase and the mature enzyme, respectively; P' and M' indicate the positions of the precursor of the truncated β-lactamase and its mature product, respectively.

In vivo processing of $\beta$-lactamase, encoded by pGD28, was examined in pulse-labeling experiments. To that purpose E.coli N4156::PGD28 was transformed with pGD40, pGDL05, pGDL06, pGDL11, pGDL12 or pGDA2, respectively. pGDA2 lacks the truncated $\beta$-lactamase gene present on the other plasmids. Transformants (Ap$^r$, Km$^r$) were selected at 42° C. M9 medium-1, containing ampicillin and kanamycin, was inoculated with single colonies and incubated at 28° C. for 21 hours. This period corresponds to approximately 7 generation times, which are necessary to dilute the SPase I in the cells far enough to become limiting (Van Dijl et al. 1988). After this period of growth at 28° C., the pulse-chase experiment was carried out. The results are presented in FIG. 6 and Table 1. In samples (taken 15 s. after the chase) of N4156::pGD28(pGDA2 or pGD40), under conditions of repressed E.coli SPase I synthesis, only the precursor form of $\beta$-lactamase (Mw 31,500) could be detected, indicating a strong reduction in the rate of processing. When the E.coli lep gene was cloned in pGD40 (pGDL05 or pGDL06), processing to mature product (Mw 29,000) occurred. However, the extent of processing depended on the orientation of the lep gene with respect to pTc$^r$. In strain N4156::pGD28(pGDL06) the processing of the $\beta$-lactamase precursor was considerably retarded as compared to that in strain N4156::pGD28(pGDL05). The fact that SPase I activity was not absent in strain N4156::pGD28(pGDL06) agrees with the observation that growth of this strain was slightly impeded. Efficient processing of pre-$\beta$-lactamase was also observed in strain N4156::pGD28 carrying pGD40 in which the 1.3 kb S.typhimurium derived lep fragment was inserted. Also in this case the extent of processing depended on the orientation of the lep fragment. The observation that in strain N4156::pGD28(pGDL11) the extent of processing pre-$\beta$-lactamase, as determined by densitometer scanning, was similar to that in strain N4156::pGD28(pGDL05) indicates that the S. typhimurium and E.coli SPases are equally efficient in the processing of the $\beta$-lactamase precursor in E.coli (Table 1). Furthermore, it is worthwhile to note that the extent of processing of the truncated pre-$\beta$-lactamase (Mw 24,000), to mature product (Mw 21,000) was determined by the level of expression of SPase I in a similar way as that of wild-type pre-$\beta$-lactamase. However, as shown in Table 1, the fraction of unprocessed truncated $\beta$-lactamase was considerably larger than that of wild-type $\beta$-lactamase, suggesting that the processing of truncated pre-enzyme was less efficient.

TABLE I*)

| plasmid | P (%) | P' (%) |
|---------|-------|--------|
| pGDA2   | 100   | —      |

TABLE I*)-continued

| plasmid | P (%) | P' (%) |
| --- | --- | --- |
| pGD40 | 100 | 100 |
| pGDL05 | 15 | 63 |
| pGDL06 | 66 | 93 |
| pGD11 | 16 | 60 |
| pGD12 | 68 | 94 |

*)Fraction unprocessed wild-type (P) and truncated (P') lactamase. This fraction was estimated as the ratio of the radioactivity incorporated in the precursor band to that incorporated in the precursor band + the mature band (× 100%).

EXAMPLE VI

Construction of Mutant Signal Sequence-Coding Regions

To test whether the overexpression of the lep gene leads to an increased processing rate of secreted proteins specific combinations of signal sequences and genes were used.

EP-A-244042 discloses randomly selected signal sequences obtained from *B. subtilis*. The sequences A2, A13, A42 and specifically modified sequences A2d and A13i were used.

The signal peptide A2 contained a "pro-like" long open reading frame between the hydrophobic core and the fusion point with the target protein. To investigate whether this very hydrophilic "pro-like" region plays a role in protein export, we have deleted the polypeptide region of 37 amino acids starting from ala (position 28) to leu (position 64), from A2 by oligonucleotide-directed site-specific mutagenesis. SEQ. ID NO 2 shows the nucleotide/amino acid sequences of signal A2d.

In contrast to A2, the signal peptide of A13 was very short. The hydrophobic core comprised only 9 amino acids. Since signal peptides from Gram-positive organisms are usually longer than those from Gram-negative organisms (von Heijne, G. and Abrahmsen, L. 1989), it is conceivable that the hydrophobic core of A13 is too short to function efficiently in *B. subtilis*. Therefore, we attempted to improve the signal peptide function of A13 by inserting 10 additional hydrophobio amino acids (position 8 to 17; SEQ ID NO: 7 and SEQ ID NO: 8) into the hydrophobic core by oligonucleotide-directed site-specific mutagenesis.

Kinetics of Processing

Figure 8:
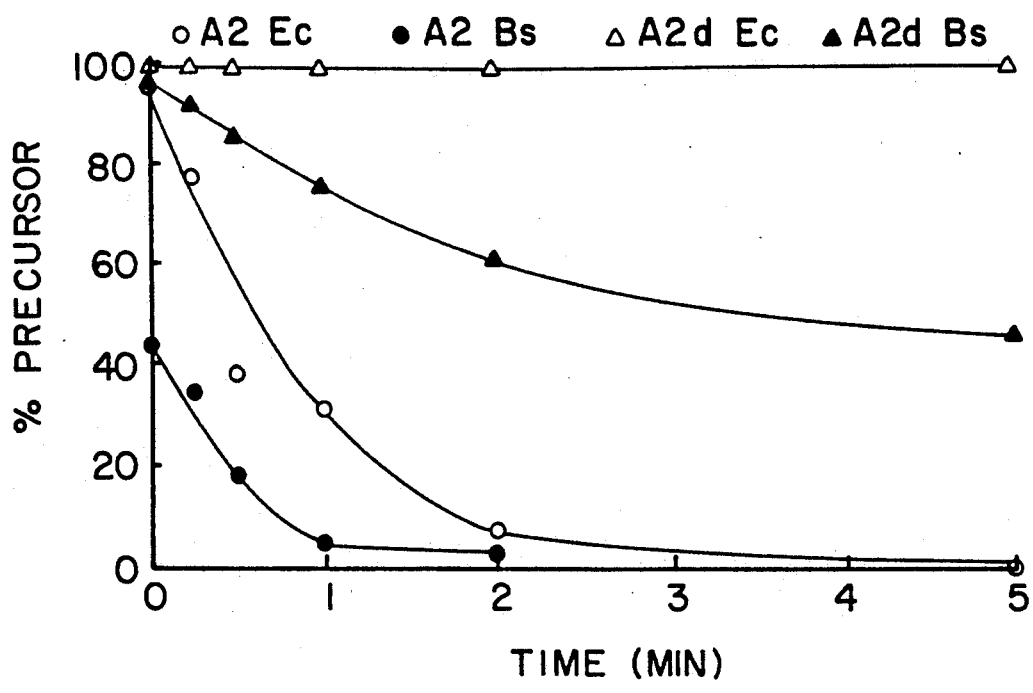
FIG. 8 shows the kinetics of processing of pre(A2)-, and pre(A2d)-β-lactamase in *B. subtilis* 8G5 or DB114 (Bs) and *E. coli* C600 (Ec). Samples were analysed by pulse-chase labeling as described (FIG. 7).

To get insight in the effects of the mutations on the efficiencies of processing during export, pulse-chase protein labeling experiments were performed. The results obtained with pre(A2d)-α-amylase and pre(A2d)-β-lactamase are shown in FIG. 7 and FIG. 8, respectively. For comparison, the kinetics of processing of pre(A2)-α-amylase and pre(A2)-β-lactamase, as determined before were included. In *B. subtilis* as well as in *E. coli* the rates of processing of pre(A2d)-α-amylase were strongly reduced compared to those of pre(A2)-α-amylase (FIG. 7). About 50% (*B. subtilis*) to 75% (*E. coli*) of the protein was still in the precursor form 5 min after the chase (FIG. 7). Qualitatively similar results were obtained with the signal peptide A2d preceding β-lactamase: the deletion in A2 strongly slowed down the kinetics of processing in both organisms (FIG. 8). In *E. coli* no processing of pre(A2d)-β-lactamase could be observed even at 60 min after the chase (results not shown). Low amounts of mature (A2d)-β-lactamase could be detected, however, by chasing overnight (FIG. 8). These data indicate that the "pro-like" region between the hydrophobic core and the fusion point with the target proteins was important for efficient processing of both pre(A2)-α-amylase and pre(A2)-β-lactamase. This result is most easily explained by the presence of a potential processing site at ala30, which was removed with the deletion in A2d.

Figure 9:
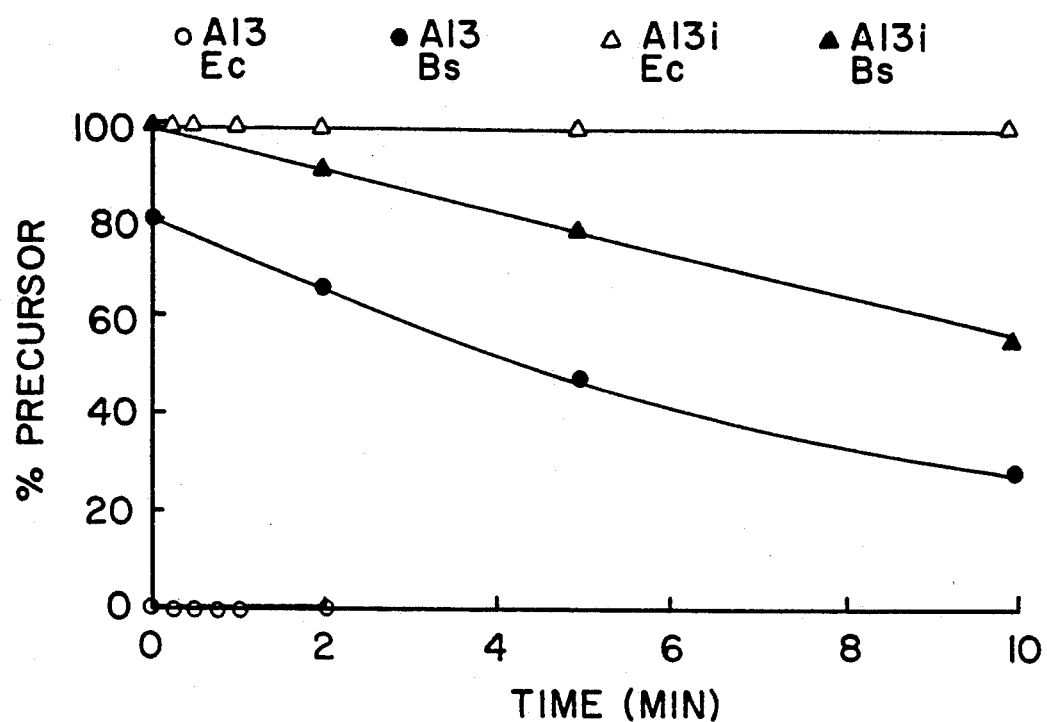
FIG. 9 shows the kinetics of processing of pre(A13)-, and pre(A13i)-α-amylase in *B. subtilis* 8G5 or DB114

In comparison to the original export function A13, A13i, containing an extended hydrophobic core, did reduce the efficiencies of processing in *B. subtilis* even further (FIG. 9 and FIG. 10). About 78% (pre[A13i]-α-amylase) to 82% (pre[A13i]-β-lactamase) of the protein was still in the precursor form 5 min after the chase. The insertion in A13i had an even more dramatic effect on the efficiency of processing of pre(13i)-α-amylase and β-lactamase in *E. coli* (FIG. 9 and FIG. 10). No mature (A13i)-α-amylase could be observed 5 min after the chase (FIG. 9). In contrast, with the original signal A13 exclusively mature (A13)-α-amylase was found 5 min after the chase (FIG. 9). In addition, no mature (A13i)-β-lactamase could be detected even after chasing overnight (data not shown). Altogether, these data show that the extension of the hydrophobic core of export function A13 had a negative effect on the efficiency of processing.

Localization of β-lactamase in *E. coli*

Despite low processing efficiencies of pre(A2d)-β-lactamase and pre(A13i)-β-lactamase, these proteins rendered *E. coli* resistant to high levels of ampicillin (Table 2).

TABLE 2

α-Amylase and β-lactamase activities in *B. subtilis* culture supernatants and ampicillin resistance in *E. coli*

| plasmid | B. subtilis α-amylase (U/ml) | plasmid | B. subtilis β-lactamase (U/ml) | E. coli amp. resist. (μg/ml) |
| --- | --- | --- | --- | --- |
| pSPA2 | 266.4 | pSPB-A2 | 18700 | 300 |
| pSPA2d | 124.4 | pSPB-A2d | 18750 | 500 |
| pSPA13 | 36.5 | pSPB-A13 | 5170 | 300 |
| pSPA13i | 23.1 | pSPB-A13i | 6160 | 100 |
| pSPA42 | 1.4 | pSPB-A42 | 2650 | 20 |
| pSpA42d | 123.4 | pSPB-A42d | 3790 | 100 |

Table 2. *B. subtilis* DB104 cultures containing pSPA or pSPB-A plasmids were grown overnight in TY or minimal medium, respectively. The α-amylase and β-lactamase activities in the culture supernatants were determined as described in Materials and Methods. Resistance to ampicillin was defined as the maximal concentration of the antibiotic at which 100% of the *E. coli* cells could form colonies. Plasmids indicated by pSPA ... contain α-amylase with the indicated signal peptide, plasmids indicated by pSPB ... contain β-lactamase with the indicated signal peptide.

The high level of ampicillin resistance suggests that at least part of the β-lactamase had been translocated across the cytoplasmic membrane. To test this, we analyzed the cellular location of β-lactamase in *E. coli* cells containing pSPB-A2d and pSPB-A13i. Table 3 shows that, like in the pulse-chase experiment, almost no free β-lactamase could be detected in the periplasm of *E. coli* cells containing pSPB-A13i. However, Table 3 (last column) shows that high levels of β-lactamase activity were found unlysed spheroplasts from cells containing pSPB-A13i. This indicates that the active protein must have been translocated across the cytoplasmic membrane.

In addition, the fractionation data showed that, although the efficiency of processing of pre(A2d)-β-lactamase was very low in *E. coli* (FIG. 8), relatively high levels of free β-lactamase could be detected in the periplasm of overnight cultures (Table 3). These data support the observation that in a pulse-chase experiment, after chasing overnight, some mature (A2d)-β-lactamase could be detected (data not shown). Apparently, processing of pre(A2d)-β-lactamase did occur, but at a very low rate.

TABLE 3

Relative β-lactamase activitites in various E. coli cell fractions

| plasmid | periplasm | cytoplasm + membranes | unlysed spheroplasts |
|---|---|---|---|
| pGB25 | 81 | 19 | 0 |
| pSPB-A2 | 75 | 25 | 3 |
| pSPB-A2d | 63 | 37 | 7 |
| pSpB-A13 | 73.9 | 26.1 | 0.5 |
| pSPB-A13i | 2.3 | 97.6 | 26 |

Table 3. Overnight cultures of E. coli carrying the various plasmids were grown in TY medium and the cells were fractionated. Entries in the columns "periplasm" and "cytoplasm" + membranes" are given as percentages of the total β-lactamase activity in cell lysates. β-Lactamase activities were measured as described in Materials and Methods. The enzymatic activities associated with unlysed spheroplasts were measured in spheroplast buffer and are also expressed as percentages of the total β-lactamase activity. As a control for lysis, the absorbance at 700 nm of the spheroplast suspension was measured before and after the assay.

EXAMPLE VII

Effects of SPase I Overproduction On Processing Kinetics

The E.coli lep gene was inserted in plasmid pBS61ΔpL and placed under the control of the repressible tac promoter, derived from pKK223.3 (De Boer et al. 1983). This resulted in plasmid pGDL2. In E.coli C600 expression of the pGDL2-encoded lep gene resulted in approximately 27-fold overproduction of SPase I, as estimated from Western blots (FIG. 11). In order to monitor any effects of SPase I overproduction in E. coli C600 the processing kinetics of four different chimeric β-lactamases were measured by pulse-chase labeling. The translocation of these chimeric β-lactamases was facilitated by signal peptides, which had been randomly selected from the chromosome of Bacillus subtilis (A2 and A42; Smith et al. 1987), and which in some cases had been altered by site directed mutagenesis (A2d and A13i, Example VI). Moreover, the effect on the processing kinetics of wild-type TEM-β-lactamase was measured as a control. To do so, strains of E.coli C600 producing these β-lactamases were transformed with pGDL2 (overproduction of SPase I) or with pBS61ΔpL (wild-type production of SPase I). The results of the pulse-chase labeling experiments are shown in FIG. 12-16. Only the processing rate of wild-type β-lactamase, which is very fast compared to the processing rates of the other β-lactamases, remained totally unaffected by SPase I overproduction (FIG. 12). Pre(A2)-β-lactamase was processed only slightly faster under conditions of SPase I overproduction (FIG. 13). The time, necessary to process 50% of the precursor ($t_{50}$) was about 20 sec reduced ($t_{50}$ under wild-type conditions = 2.5 minutes, $t_{50}$ under conditions of SPase I overproduction = 2.2 minutes). In all other examples processing kinetics appeared to be more clearly affected by SPase I overproduction: Pre(A42)-β-lactamase showed a clearly increased rate of processing (FIG. 14), the $t_{50}$ of this precursor was reduced with 11 minutes by SPase I overproduction ($t_{50}$ under wild-type conditions = 26 minutes, $t_{50}$ under conditions of SPase I overproduction = 15 minutes). However, the most extreme effect could be measured with pre(A2d)-β-lactamase. This precursor, which is processed very slowly in E. coli C600 under wild-type conditions (see Example VI) showed a dramatically increased rate of processing under conditions of SPase I overproduction (FIG. 15). The $t_{50}$ of pre(A2d)-β-lactamase could not be measured under wild-type conditions because of the slow processing rate (Smith et al. data not shown). By SPase I overproduction the processing rate was so much increased, that about 65% of the precursor had already been processed within 1 minute of labeling ($t_{50}$ under conditions of SPase I overproduction < 1 minute). The possibility of a mutation in the signal sequence of pre(A2d)-β-lactamase causing the effect measured could be ruled out. Transformation of E.coli C600 with pSPB-A2d, extracted from the SPase I overproducing strain, and subsequent pulse-chase analysis revealed slow processing kinetics again (data not shown). Processing of pre-(A13i)-β-lactamase was also affected by SPase I overproduction. In contrast to the other three chimeric β-lactamases, processing of this precursor was not detectable at all under wild-type condition (see Example VI). However, under conditions of SPase I overproduction a small amount of mature enzyme was detectable (FIG. 16). The mature enzyme appeared directly after the chase and its relative amount (6 to 7% of all the (A13i)-β-lactamase synthesized) remained almost unaltered during the period of sampling (chase). This indicates that, although only a minor fraction of the pre(A1-3i)-β-lactamase was processed, the rate of processing was very high.

Effects of SPaseI Overproduction on the Localization of Precursors and Mature Enzymes Proteolytic processing of the precursors of translocated proteins by SPases in E. coli is considered to be a prerequisite for the release of the mature enzyme into the periplasm (Dalbey and Wickner 1985). It was therefore of interest to study the localization of the slowly processed export proteins used in these investigations (pre[A2d]-β-lactamase and pre[A13i]-β-lactamase), which were sensitive to SPase I overproduction. The localization of precursors and mature products was determined by pulse-chase labeling of proteins, followed by spheroplasting, and subsequent separation of spheroplasts and periplasmic contents by centrifugation.

Processing of wild-type β-lactamase (the samples were taken 90 sec after the chase) could not be stopped instantaneously by chilling on ice, as revealed by the fact that no precursor could be detected. The mature β-lactamase fractionated with the periplasmic contents, which was not affected by SPase I overproduction (data not shown).

The localization of pre(A2)-β-lactamase and its mature product was determined in samples taken 2 minutes after the chase. Although, as with wild-type pre-β-lactamase, processing was not stopped instantaneously, a significant amount of pre(A2)-β-lactamase was detectable, presumably as a consequence of the fact that pre-(A2)-β-lactamase is processed slower than the wild-type pre-β-lactamase. The pre(A2)-β-lactamase appeared to be exclusively associated with the spheroplast fraction, whereas most of the mature product (94%) was present in the periplasmic fraction. These results were not altered by SPase I overproduction (data not shown).

The level of SPase I production clearly affected the localization of (A2d)-β-lactamase in samples taken 5 min after the chase (37° C.). Although, as with pre(A2)-β-lactamase, pre(A2d)-β-lactamase was associated exclusively with the spheroplasts, due to the increased rate of pre(A2d)-β-lactamase processing under conditions of SPase I overproduction, a highly increased amount of mature enzyme could be detected in the periplasmic fraction. These results indicate that overproduction of SPase I not only resulted in a drastic increase in the rate of pre(A2d)-β-lactamase processing, but also in a concomitant increase in the rate of release of the mature enzyme into the periplasm. These results are in full agreement with the idea (Dalbey and Wickner, 1985) that proteolytic processing of the precursor is required for the release of the mature protein into the periplasm.

Fractionation of cells containing (A13i)-β-lactamase showed a different pattern. Under all conditions tested, pre(A13i)-β-lactamase remained associated with the spheroplasts. However, unexpectedly, a major fraction of the mature enzyme, detectable only under conditions of SPase I overproduction, was also associated with the spheroplast fraction. Only about 20% of the mature enzyme, representing less than 2% of the total amount of (A13i)-β-lactamase synthesized, was detectable in the periplasmic fraction. It remains uncertain whether this small periplasmic fraction resulted from true release into the periplasm as a consequence of SPase I processing or from lysis of a small fraction of the spheroplasts.

EXAMPLE VIII

Assay for Processing of β-Lactamase Precursors on Plates

The export characteristics of various hybrid proteins consisting of mature E. coli TEM-β-lactamase, which was fused to signal peptides randomly selected from the B. subtilis chromosome have been described (Smith et al., 1987; Smith et al., 1988). One of these signal peptides, designated A13, efficiently directed the export of β-lactamase into the growth medium in B. subtilis (secretion), and into the periplasm in E. coli (Smith et al., 1988; van Dijl et al., 1990). The extension of the hydrophobic h-region of signal peptide A13 with 10 hydrophobic amino acids, resulting in signal peptide A13i, greatly reduced its efficiency in directing the export of β-lactamase in both organisms. In E.coli the unprocessed pre(A13i)-β-lactamase was translocated across the cytoplasmic membrane to which it remained attached. Being exposed into the periplasm, the unprocessed protein gave rise to high levels of ampicillin resistance. A minor fraction of the pre(A13i)-β-lactamase was processed under conditions of SPase I overproduction in E. coli (van Dijl et al., 1990), therefore, the observed export-defect of pre(A13i)-β-lactamase in E. coli could be attributed to the lack of productive interaction with SPase I. In contrast, mature (A13i)-β-lactamase was secreted in B. subtilis suggesting that the SPase I of this organism was capable of recognizing and processing the precursor (Smith et al., 1990). To identify the component of the B. subtilis export machinery, which was responsible for the processing of pre(A13i)-β-lactamase a plate assay (halo formation) for the detection of β-lactamase activity in E. coli colonies was used. Halo formation around colonies can only be successful if at least some mature TEM-β-lactamase can leak from the periplasm into the growth medium. A zone of decoloration (halo) due to β-lactamase activity could be demonstrated around colonies producing the rapidly processed (A13)-β-lactamase, indicating that, like the wild-type β-lactamase (Georgiou et al., 1988), this hybrid β-lactamase could also leak from the periplasm of E. coli. In contrast, no halo could be demonstrated around colonies producing the unprocessed pre(A13i)-β-lactamase, indicating that this precursor could not leak from the cells into the surrounding agar medium. Thus, halo formation apparently correlated with processing and release of the mature β-lactamase into the periplasm.

Selection of Halo-forming Transformants Containing B. subtilis DNA Shotgun Cloned in pSBA13i The potential of the above described halo assay in E. coli for the cloning of the factor which is required for the processing of pre(A13i)-β-lactamase in B. subtilis, was tested next. The cloning and expression of the gene encoding this factor in E. coli is expected to give rise to colonies capable of processing pre(A13i)-β-lactamase, provided that the product is functional. Using the halo assay it should be possible to identify these colonies. To that purpose chromosomal B. subtilis DNA was partially digested with Sau3A. This DNA was used for cloning into BclI-cleaved pSBA13i (as pSPB-A13i, however the pTA1060 replication functions were replaced by those of pWVO1) which had been treated with alkaline phosphatase. After (electro)transformation, 26.000 ampicillin-resistant transformants were tested for the ability to produce halos. The total collection of recombinant pSBA13i plasmids contained cloned DNA fragments with a total size equivalent to approximately 13 times the B. subtilis genome. Thirteen halo-forming transformants could be detected.

Restriction analysis showed that the plasmids in these transformants contained two types of inserted fragments, one of which (fragment A) was present in 12 clones on overlapping Sau3A fragments. The smallest of these fragments (2.4 kb) contained an internal 2.1 kb HindIII fragment. The size of the other fragment (B) appeared to be approximately 700 bp. pSBA13i, containing fragment B was named pGDL40. Transformants containing either fragment A, or fragment B, gave only rise to halo's when the overlayer contained ampicillin, indicating that halo formation was due to β-lactamase activity (data not shown). Furthermore, halo formation was not due to mutations in the signal sequence A13i. This was shown by isolating the DNA fragment encoding A13i from the transformants and ligating it to the truncated β-lactamase gene of the signal sequence-selection vector pGPB14. None of the resulting transformants showed β-lactamase halo formation (data not shown).

Processing of pre(A13i)-β-lactamase

In order to examine whether halo formation was due to the processing of pre(A13i)-β-lactamase, pulse-chase labeling experiments were performed. Only when fragment B was present in pSBA13i, processing of pre(A13i)-β-lactamase was observed. The cellular localization of the mature (A13i)-β-lactamase was determined by pulse-chase labeling of proteins, followed by spheroplasting, and subsequent separation of spheroplasts and periplasmic contents. As expected, the mature enzyme fractionated with the periplasmic contents. These data show that fragment B encoded the factor, which was responsible for the processing of pre(A13i)-β-lactamase in B. subtilis.

In contrast, no processing of pre(A13i)-β-lactamase was detectable when pSBA13i carried fragment A (data not shown).

EXAMPLE IX

DNA Sequence Analysis of the *Bacillus subtilis* Lep Gene

In order to determine whether fragment B contained the *B. subtilis* lep gene, encoding SPase I, the complete fragment cloned in pGDL40 was sequenced. The results showed that this fragment consisted of two Sau3A fragments of 97 bp and 696 bp, respectively (see Sequence Listing, SEQ ID NO:9 and SEQ. ID NO: 10). Analysis of the sequence revealed the presence of one open reading frame (ORF, bases 239-793), which can encode a protein (consisting of 184 amino acids) with a calculated Mw of 21,032. The ORF was preceded by a potential Shine-Dalgarno sequence (GGAGG) with a dG = −14.4 kcal (Tinoco et al., 1973), and with a spacing of 10 bases with respect to the putative start codon (TTG). In order to identify this ORF, its deduced amino acid sequence was compared to amino acid sequences in the Database. Significant similarities were only found with the SPase I of *E. coli* (FIG. 17) and *S. typhimurium*. Therefore, we conclude that the sequenced DNA fragment, which is responsible for the in vivo processing of pre(A13i)-β-lactamase in *E. coli* contains the gene encoding the SPase I of *B. subtilis*.

The similarities between the enzymes were mainly located in three different regions. The first region of similarity (amino acids 6-57 of the *B. subtilis* SPase I/amino acids 53-103 of the *E. coli* SPase I; 28.3% identity) overlaps with two domains of *E. coli* SPase I designated H2 and H3, one of which (H2) functions as an internal uncleaved internal signal peptide (Dalbey et al., 1987); Zhu and Dalbey 1989). The other two regions of similarity (amino acids 59-93 of the *B. subtilis* SPase I/amino acids 118-155 of the *E. coli* SPase I; 47.4% identity, and amino acids 136-155 of the *B. subtilis* SPase I/amino acids 263-282 of the *E. coli* SPase I; 70% identity, respectively correspond to amino acid sequences of the *E. coli* SPase I, which are exposed to the outer surface of the cytoplasmic membrane (Moore and Miura 1987; Wolfe et al., 1983). By analogy with the lep gene encoding the SPase I of *E. coli*, the gene encoding the *B. subtilis* SPase I will, be referred to as lepBS.

The comparison between the *E. coli* and *B. subtilis* SPase I proteins also revealed an interesting difference. Whereas the *E. coli* SPase I contains two membrane spanning regions, the first of these regions (amino acids 1-22), referred to as H1 (Dalbey et al., 1987), appeared to be absent from the *B. subtilis* SPase I. This might be due to a specific deletion that had occurred during the cloning of fragment B in pSBA13i. Although we considered this possibility unlikely since enzymatic activity was observed in *E. coli*, this possibility was further investigated. *B. subtilis* chromosomal DNA was digested with Sau3A and analysed by Southern blotting using the 696-bp Sau3A fragment containing the lepBS gene as a hybridization probe. The hybridizing Sau3A fragment of the *B. subtilis* chromosomal DNA had the same size as the cloned fragment, which was used as a probe (data not shown). This indicates that it was very unlikely that a deletion of approximately 66 bp (encoding H1) had occurred. Therefore, we conclude that region H1 was indeed absent from the *B. subtilis* SPase I.

In vitro transcription and translation of pGDL40 showed that fragment B encoded a protein with an apparent Mw of 21,000 dalton. This is in good agreement with the calculated Mw of 21,032 for the *B. subtilis* SPase I encoded by lepBS.

EXAMPLE X

Hybridization Experiments Using the *Bacillus subtilis* LepBS Gene as a Probe The cloned *B. subtilis* leader peptidase gene (lep BS) was used as a probe to detect homologous genes in several other Bacillus species, as well as in a number of other microorganisms.

Chromosomal DNA was isolated from the following species, using standard procedures; *B. subtilis, B. licheniformis, B. amyloliquefaciens,* and *B. alcalophilus*. The DNA's were seperately digested with the following restriction endonucleases: EcoRI, HindIII, and PstI, and size fractionated on 0.8% agarose gels. Subsequently, the DNA fragments were transferred and immobilized on Genescreen filters.

An 0.3 kb DNA fragment, encoding the N-terminal part of the Bacillus leader peptidase, was obtained using the Polymerase Chain Reaction method. The following oligonucleotides were used:

a) 5'-GGGCAAAAGCAATTGTG-3', SEQ ID NO: 1 b) 5'-CGTCCTGTTTCGCTCTC-3', SEQ ID NO: 2 as primers and pGDL40 as template.

The resulting fragment was labelled with $^{32}$P by nick-translation and hybridized with the immobilized chromosomal DNA digests in 3×SSC at 65° C. for 16 hours. Subsequent washing of the blots was performed in 3×SSC, 0.1% SDS at 25° C. The blots were dried and exposed to X-ray film for 24 hours.

The results of this experiment are shown in FIG. 18 Discrete hybridizing fragments are observed for *B. subtilis B. licheniformis, B. amyloliquefaciens* and *B. alcalophilus*.

EXAMPLE XI

Overexpression of the *Bacillus subtilis* lepBS Gene in Bacillus

In *E. coli* the processing efficiency of pre(A13i)-β-lactamase could be improved by overproduction of SPase I, which indicated that the availability of SPase I was limiting under standard conditions. Since the pre-(A13i)-β-lactamase is processed very slowly in *B. subtilis* (Example VI and VII) it was assumed that also in this organism the availability of SPase I might be limiting under standard conditions. In order to address this question, the lepBS gene was introduced in *B. subtilis* DB104 (Kawamura and Doi (1984)) on plasmid pGDL41 (FIG. 19). This plasmid is a derivative of pGDL40 containing a selectable marker (Km$^r$) for *B. subtilis*. pGDL41 and pGDL42 were constructed by replacing the 0.3-kb EcoRI fragment containing the SPO2 promoter of pGDL40 and pSBA13i, respectively, by a 1.4-kb EcoRI fragment of pKM1 (Kiel et al., 1987) containing a *Streptococcus faecalis* Km$^r$ gene.

The effect of the increased lepBS gene dosis in *B. subtilis* DB104(pGDL41) on the processing kinetics of pre(A13i)-β-lactamase was studied by pulse-chase labeling experiments. As a control (standard conditions) pulse-chase labeling experiments were performed with *B. subtilis* DB104 transformed with plasmid pGDL42 (FIG. 19), lacking the lepBS gene. The results show that the processing kinetics of pre(A13i)-β-lactamase were clearly affected by SPase I overproduction.

Under standard conditions (*B. subtilis* DB104[pGD142]) pre(A13i)-β-lactamase was processed slowly: at t=0 no mature (A13i)-β-lactamase could be observed (FIG. 20 B, D, and E) and the time necessary to obtain equal amounts of the precursor and the mature forms of (A13i)-β-lactamase ($t_{50}$) was approximately 10 min (FIG. 20 D and E). The initial rate of pre(A13i)-β-lactamase processing was highly increased under conditions of SPase I overproduction (*B.subtilis* DB104[pGDL41]; FIG. 20 A,C, and E): about 20% (±5% in various experiments; FIG. 20 A and C) of the total (A13i)-β-lactamase present was already mature after 1 min labeling, and the $t_{50}$ was approximately 6 min (FIG. 20 C and E). These data indicate that, like in *E.coli*. in *B.subtilis* under standard conditions the availability of SPase I is rate limiting for the processing of pre(A13i)-β-lactamase.

EXAMPLE XII

Mutagenesis of the *B. subtilis* SPase

Comparison of the amino acid sequences of the *B. subtilis*, *E. coli* and *Salmonella typhimurium* SPase I with the Database revealed a short region of similarity with the SEC11 protein of *Saccharomyces cerevisiae* (Böhni et al, 1988) and the canine 21K protein (Greenburg et al, 1989) (FIG. 21). The latter two proteins are components of the signal peptidase complexes of *S. cerevisiae* and dog, respectively. Hence, this region appears to be conserved in all five SPases described so far. In the SPase I of *E. coli* the conserved region is located in a domain of the enzyme, which is believed to be essential for the catalytic activity. It is therefore probable that the conserved amino acids from part of the catalytic site of SPases. Especially, the conserved Serine and Aspartic acid residues (marked * in FIG. 21) are highly interesting, since these amino acid residues, together with a Histidine residue, form the catalytic triad of serine proteases. This raises the question whether SPases are related to this group of proteinases. It is therefore conceivable that the differences within the conserved region of these five proteins may account for their different specificities (Von Heijne and Abrahmsén, 1989). The three conserved regions are also underlined in the lepBS sequence in SEQ ID NO:9 and SEQ ID NO: 10.

To elucidate the function of the conserved region in activity and specificity of SPases various mutations can be introduced into the corresponding region of the *B. subtilis* SPase I. These mutations can include either the partial or complete exchange of the (non-)conserved amino acids. Alternatively, mutations can be introduced at random, using spiked oligonucleotides of approximately 100 bases. Before starting the actual mutagenesis, two unique restriction sites will be introduced in pGDL40. A SmaI site will be introduced just before the Shine-Dalgarno sequence of the lepBS gene (position 215, SEQ. ID NO: 9 and SEQ ID NO: 10). A SalI site will be introduced in the region of the lepBS gene encoding the amino acid residues which are conserved in the various SPases (position 353; SEQ. ID NO:9 and SEQ ID NO:10). Using these two restriction sites, mutations created with the aid of PCR techniques can be introduced in the lepBS gene. Mutant SPases with altered specificity or activity can be detected with the aid of the halo assay for pre(A13i)-β-lactamase-processing activity. Mutations causing the inactivation of the enzyme can be identified with the aid of *E. coli* N415G::pGD28(pBS61dp) in which the expression of SPase I can be repressed (van Dijl et al, 1987). Repression of the chromosomally located lep gene of this strain results in non-viability. This growth inhibition can only be suppressed when the strain is transformed with plasmids containing mutated lep genes that encode active SPases.

A similar approach as described above can also be used for the mutagenesis of the *E. coli* SPase I.

Both the mutagenesis of the *B. subtilis* and the *E. coli* SPases will lead to new SPases with different specificities and altered activities. The potential of these newly created SPases to improve the export of heterologous proteins in *E. coli*, *B. subtilis* and other bacilli can be examined.

REFERENCES

Anba, J., C. Lazdunski, J.-M. Pages. 1986. J. Gen. Microbiol. 132, 689–696.

Ausubel, F. A. et al. 1987. Current protocols in Molecular Biology. J. Wiley and Sons Inc. New York.

Bieker, K. L. and T. J. Silhavy. 1990. Trends in Genetics 6, 329–334.

Böhni, P. C., R. J. Deshaies and R. W. Schekman. 1988. J. Cell. Biol. 106, 1035–1042.

Chevallier, M. R. and M. Aigle. 1979. FEBS Lett. 108, 179–180.

Dalbey, R. E. and W. Wickner. 1985. J. Biol. Chem. 260, 15925–15931.

Dalbey, R. E., Kuhn, A. and W. Wickner. 1987. J. Biol. Chem. 262, 13241–13245.

Date, T. and W. Wickner. 1981. Proc. Natl. Acad. Sci. U.S.A. 78, 6106–6110.

DeBoer, H. A., J. L. Comstock and M. Vasser. 1983. Proc. Natl. Aca. Sci. U.S.A. 80, 21–25.

Edens, L., L. Heslinga, R. Klok, A. M. Ledeboer, J. Maat, M. Y. Toonen, C. Visser and C. T. Verrips. 1982. Gene 18, 1–12.

Fahnestock, S. R. and K. E. Fisher. 1987. Appl. Environm. Microbiol. 53, 379–384.

Georgiou, G., Schuler, M. L. and D. B. Wilson. 1988. Biotechnol. and Bioeng. 32, 741–748.

Greenburg, G., G. S. Shelness and G. Blobel. 1989. J. Biol. Chem. 264, 15762–15765.

Hermes et al. 1989. Gene 84, 143–151.

Kawamura, F. and R. H. Doi. 1984. J. Bacteriol. 160, 442–444.

Kiel, J. A. K. W., Vossen, J. P. M. J., and G. Venema. 1987. Mol. Gen. Genet. 207:294–301.

Laemmli. U. K. 1970. Nature 227, 680–685.

Lampen. J. O., F. I. J. Pastor and M. Hussain. 1986. Microbiology 279–282. Washington D.C., U.S.

Maniatis, T., E. F. Fritsch and J. Sambrook. 1982. Molecular Cloning: a laboratory manual. Cold Spring Harbor Laboratory, Cold Spring Harbor, N.Y.

March, P. E. and M. Inouye. 1985. J. Biol. Chem. 260, 7206–7212.

Moore, K. E. and S. Miura. 1987. J. Biol. Chem. 262, 8806–8813.

Palva I. 1989. Engineering for secretion of proteins by bacteria. 255–269. In: Microbial Products: New Approaches. 44th Symposium of the Society for General Microbiology. Ed. S. Baumberg, I. Hunter and M. Rhodes. Cambridge Univ.Press. Cambridge U.K.

Skinner, M. K. and M. D. Griswold. 1983. Biochem. J. 209, 281–284.

Sloma, A., A. Ally, D. Ally and J. Pero. 1988. J. Bacteriol. 170, 5557-5563.

Smith, H., S. Bron, J. van Ee and G. Venema. 1987. J. Bacteriol. 169, 3321-3328.

Smith, H., A. de Jong, S. Bron and G. Venema. 1988. Gene 70, 351-361.

Tinoco, I., Borer, P. N., Dengler, B., Levine, M. D., Uhlenbeck, O. C. Crothers, D. M. and J. Gralla. 1973. Nature 246, 40-41.

Tokunaga M., J. M. Loranger, P. B. Wolfe and H. C. Wu. 1982. J. Biol. Chem. 257, 9922-9925.

Towbin, H., T. Staehelin and J. Gordon. 1979. Proc. Natl Acad. Sci. U.S.A. 76, 4350-4354.

Van Dijl, J. M., H. Smith, S. Bron and G. Venema. 1988. Mol. Gen. Genet. 214, 55-61.

Van Dijl et al. 1990. Mol. Gen. Gen. 223, 233-240.

Vasantha, N. and E. Freese. 1980. J. Bacteriol. 144, 1119-1125.

Von Heijne, G. and L. Abrahmsen. 1989. FEBS Lett. 244, 439-446.

Wolfe, P. B., P. Silver and W. Wickner. 1982. J. Biol. Chem. 257, 7898-7902.

Wolfe, P. B., W. Wickner and J. M. Goodman. 1983. J. Biol. Chem. 258, 12073-12080.

Yamada, H., H. Yamagata and S. Mizushima. 1984. FEBS Lett. 166, 179-182.

Yamagata, H., C. Ippolito, M. Inukai and M. Inouye. 1982. J. Bacteriol. 152, 1163-1168.

Zhu, H. and R. E. Dalbey. 1989. J. Biol. Chem. 264, 11833-11838.

---

We claim:

1. An isolated DNA consisting essentially of DNA encoding a type I SPase (signal peptidase) from a Bacillus microorganism.

2. A DNA according to claim 1, wherein the microorganism is *Bacillus subtilis*.

3. An isolated DNA fragment that hybridizes with the DNA of claims 1 or 2 under stringent conditions and that encodes an enzyme which exhibits type I SPase proteolytic activity.

4. A method of obtaining a periplasmic outer membrane or secreted protein comprising culturing a prokaryotic host cell transformed with a SPase I gene derived from *Salmonella typhimurium* or Bacillus under conditions favoring expression of said gene in order to obtain increased processing activity of a periplasmic, outer membrane or secreted protein with respect to the corresponding parental host cell or with respect to a host cell in which said protein is normally unprocessed or processed with difficulty.

5. A transformed prokaryotic host cell capable of increasing the processing activity of a periplasmic, outer membrane or secreted protein with respect to the corresponding parental host cell or with respect to a host cell in which said protein is normally unprocessed or processed with difficulty containing A) an expression vector encoding a type I SPase derived from *Salmonella typhimurium* and Bacillus and a desired periplasmic, outer membrane or secreted protein, or B) two expression vectors, the first encoding a type I SPase derived from Salmonella or Bacillus and the second encoding a desired periplasmic, outer membrane or secreted protein.

6. A transformed prokaryotic host cell wherein a SPase I gene derived from *Salmonella typhimurium* or Bacillus is overexpressed resulting in increased processing activity of a periplasmic, outer membrane or secreted protein with respect to the corresponding parental host cell or with respect to a host cell in which said protein is normally unprocessed or processed with difficulty.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGGCAAAAGC AATTGTG          17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGTCCTGTTT CGCTCTC          17

( 2 ) INFORMATION FOR SEQ ID NO:3:

( i ) SEQUENCE CHARACTERISTICS:
        ( A ) LENGTH: 1294 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(1..105, 125..1096)

( x i ) SEQUENCE DESCRIPTION: SEQ ID NO:3:

```
CTG CAG AAA CAG AAA GAA GGT AAG AAA CGC ATG AAG CAG ATC GGT AAC        48
Leu Gln Lys Gln Lys Glu Gly Lys Lys Arg Met Lys Gln Ile Gly Asn
 1               5                  10                  15

GTC GAG CTG CCT CAG GAA GCG TTC CTC GCC ATT CTG CAT GTC GGT AAA        96
Val Glu Leu Pro Gln Glu Ala Phe Leu Ala Ile Leu His Val Gly Lys
            20                  25                  30

GAC AAT AAA TAATCCCTAA GGAGTTGGC ATG GCG AAC ATG TTT GCC CTG ATT      148
Asp Asn Lys                         Met Ala Asn Met Phe Ala Leu Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 35  |     |     |     |     |     |     |     |     | 40  |     |     |      |
| CTG | GTG | ATA | GCC | ACA | CTG | GTG | ACG | GGC | ATT | TTA | TGG | TGC | GTT | GAT | AAG | 196  |
| Leu | Val | Ile | Ala | Thr | Leu | Val | Thr | Gly | Ile | Leu | Trp | Cys | Val | Asp | Lys |      |
|     |     | 45  |     |     |     | 50  |     |     |     |     | 55  |     |     |     |     |      |
| TTT | GTT | TTC | GCG | CCA | AAA | CGT | CGG | GCG | CGC | CAG | GCT | GCC | GCG | CAA | ACG | 244  |
| Phe | Val | Phe | Ala | Pro | Lys | Arg | Arg | Ala | Arg | Gln | Ala | Ala | Ala | Gln | Thr |      |
| 60  |     |     |     |     | 65  |     |     |     |     | 70  |     |     |     |     | 75  |      |
| GCG | TCG | GGA | GAT | GCG | CTG | GAT | AAC | GCT | ACG | CTC | AAT | AAA | GTG | GCG | CCT | 292  |
| Ala | Ser | Gly | Asp | Ala | Leu | Asp | Asn | Ala | Thr | Leu | Asn | Lys | Val | Ala | Pro |      |
|     |     |     |     | 80  |     |     |     |     | 85  |     |     |     |     | 90  |     |      |
| AAG | CCG | GGC | TGG | CTG | GAG | ACT | GGG | GCG | TCG | GTT | TTC | CCG | GTT | CTG | GCG | 340  |
| Lys | Pro | Gly | Trp | Leu | Glu | Thr | Gly | Ala | Ser | Val | Phe | Pro | Val | Leu | Ala |      |
|     |     |     | 95  |     |     |     |     | 100 |     |     |     |     | 105 |     |     |      |
| ATC | GTT | CTG | ATC | GTT | CGT | TCA | TTT | CTT | TAT | GAA | CCC | TTT | CAG | ATC | CCG | 388  |
| Ile | Val | Leu | Ile | Val | Arg | Ser | Phe | Leu | Tyr | Glu | Pro | Phe | Gln | Ile | Pro |      |
|     |     | 110 |     |     |     |     | 115 |     |     |     |     | 120 |     |     |     |      |
| TCA | GGC | TCA | ATG | ATG | CCG | ACA | CTG | CTT | ATC | GGC | GAT | TTT | ATT | CTG | GTG | 436  |
| Ser | Gly | Ser | Met | Met | Pro | Thr | Leu | Leu | Ile | Gly | Asp | Phe | Ile | Leu | Val |      |
|     | 125 |     |     |     |     | 130 |     |     |     |     | 135 |     |     |     |     |      |
| GAA | AAA | TTT | GCC | TAC | GGC | ATT | AAA | GAT | CCG | ATC | TAC | CAG | AAA | ACC | CTG | 484  |
| Glu | Lys | Phe | Ala | Tyr | Gly | Ile | Lys | Asp | Pro | Ile | Tyr | Gln | Lys | Thr | Leu |      |
| 140 |     |     |     |     | 145 |     |     |     |     | 150 |     |     |     |     | 155 |      |
| ATT | GAG | ACC | GGT | CAT | CCA | AAG | CGC | GGG | GAT | ATT | GTG | GTA | TTT | AAA | TAT | 532  |
| Ile | Glu | Thr | Gly | His | Pro | Lys | Arg | Gly | Asp | Ile | Val | Val | Phe | Lys | Tyr |      |
|     |     |     |     | 160 |     |     |     |     | 165 |     |     |     |     | 170 |     |      |
| CCG | GAA | GAT | CCT | AAG | TTA | GAT | TAC | ATC | AAA | CGC | GCC | GTC | GGT | TTG | CCG | 580  |
| Pro | Glu | Asp | Pro | Lys | Leu | Asp | Tyr | Ile | Lys | Arg | Ala | Val | Gly | Leu | Pro |      |
|     |     |     | 175 |     |     |     |     | 180 |     |     |     |     | 185 |     |     |      |
| GGC | GAT | AAA | ATC | ACT | TAT | GAT | CCG | GTT | GCG | AAA | GAG | GTG | ACG | ATT | CAG | 628  |
| Gly | Asp | Lys | Ile | Thr | Tyr | Asp | Pro | Val | Ala | Lys | Glu | Val | Thr | Ile | Gln |      |
|     |     | 190 |     |     |     |     | 195 |     |     |     |     | 200 |     |     |     |      |
| CCT | GGC | TGT | AGC | TCC | GGT | CAG | GCG | TGC | GAA | AAT | GCG | CTG | CCG | GTT | ACC | 676  |
| Pro | Gly | Cys | Ser | Ser | Gly | Gln | Ala | Cys | Glu | Asn | Ala | Leu | Pro | Val | Thr |      |
|     | 205 |     |     |     |     | 210 |     |     |     |     | 215 |     |     |     |     |      |
| TAC | TCT | AAC | GTT | GAG | CCG | AGC | GAT | TTT | GTA | CAG | ACT | TTT | GCC | CGC | CGT | 724  |
| Tyr | Ser | Asn | Val | Glu | Pro | Ser | Asp | Phe | Val | Gln | Thr | Phe | Ala | Arg | Arg |      |
| 220 |     |     |     |     | 225 |     |     |     |     | 230 |     |     |     |     | 235 |      |
| AAC | GGC | GGA | GAA | GCG | ACC | AGC | GGT | TTT | TTT | GAA | GTT | CCG | CTA | AAC | GAG | 772  |
| Asn | Gly | Gly | Glu | Ala | Thr | Ser | Gly | Phe | Phe | Glu | Val | Pro | Leu | Asn | Glu |      |
|     |     |     |     | 240 |     |     |     |     | 245 |     |     |     |     | 250 |     |      |
| ACG | AAA | GAA | AAC | GGC | ATT | CGC | CTG | ACC | GAA | CGT | AAA | GAG | ACG | TTG | GGC | 820  |
| Thr | Lys | Glu | Asn | Gly | Ile | Arg | Leu | Thr | Glu | Arg | Lys | Glu | Thr | Leu | Gly |      |
|     |     |     | 255 |     |     |     |     | 260 |     |     |     |     | 265 |     |     |      |
| GAT | GTG | ACG | CAC | CGC | ATC | CTG | ATG | GTG | CCG | ATA | GCT | CAG | GAT | CAG | TTG | 868  |
| Asp | Val | Thr | His | Arg | Ile | Leu | Met | Val | Pro | Ile | Ala | Gln | Asp | Gln | Leu |      |
|     |     | 270 |     |     |     |     | 275 |     |     |     |     | 280 |     |     |     |      |
| GGC | ATG | TAT | TAC | CAA | CAG | CCA | GGA | CAA | CCG | CTG | GCG | ACC | TGG | GTT | GTA | 916  |
| Gly | Met | Tyr | Tyr | Gln | Gln | Pro | Gly | Gln | Pro | Leu | Ala | Thr | Trp | Val | Val |      |
|     | 285 |     |     |     |     | 290 |     |     |     |     | 295 |     |     |     |     |      |
| CCG | CCG | GGA | CAA | TAT | TTC | ATG | ATG | GGC | GAC | AAC | CGC | GAT | AAC | AGC | GCG | 964  |
| Pro | Pro | Gly | Gln | Tyr | Phe | Met | Met | Gly | Asp | Asn | Arg | Asp | Asn | Ser | Ala |      |
| 300 |     |     |     |     | 305 |     |     |     |     | 310 |     |     |     |     | 315 |      |
| GAT | AGC | CGT | TAC | TGG | GGA | TTT | GTT | CCG | GAA | GCG | AAT | CTG | GTC | GGT | AAA | 1012 |
| Asp | Ser | Arg | Tyr | Trp | Gly | Phe | Val | Pro | Glu | Ala | Asn | Leu | Val | Gly | Lys |      |
|     |     |     |     | 320 |     |     |     |     | 325 |     |     |     |     | 330 |     |      |
| GCG | GTC | GCT | ATC | TGG | ATG | AGC | TTT | GAC | AAG | CAG | GAA | GGG | GAG | TGG | CCG | 1060 |
| Ala | Val | Ala | Ile | Trp | Met | Ser | Phe | Asp | Lys | Gln | Glu | Gly | Glu | Trp | Pro |      |
|     |     |     | 335 |     |     |     |     | 340 |     |     |     |     | 345 |     |     |      |
| ACA | GGC | GTA | CGC | CTG | AGT | CGT | ATC | GGC | GGT | ATT | CAC | TAACTGTGAT |     |     |     | 1106 |
| Thr | Gly | Val | Arg | Leu | Ser | Arg | Ile | Gly | Gly | Ile | His |     |     |     |     |      |
|     | 350 |     |     |     |     |     | 355 |     |     |     |     |     |     |     |     |      |

-continued

```
GAAATGATCG TTCACGCTGC CGTCTTTTTA GCGGCAGCGT GAATTATTTC CTGGATAAAT      1166

TCCCTAAGAC TAACGACATC CCCTGTCGTT GTGTATAGAA TATTCCCCCG AAGTTTTAGG      1226

TTGGCGCCGT TTGGTCGCCA CGGCACACGA AACAGCGTTG GTTATAGACA ACCTTCTTTC      1286

CGCTGCAG                                                               1294
```

(2) INFORMATION FOR SEQ ID NO:4:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:4:

```
Leu Gln Lys Gln Lys Glu Gly Lys Lys Arg Met Lys Gln Ile Gly Asn
 1               5                  10                  15

Val Glu Leu Pro Gln Glu Ala Phe Leu Ala Ile Leu His Val Gly Lys
            20                  25                  30

Asp Asn Lys Met Ala Asn Met Phe Ala Leu Ile Leu Val Ile Ala Thr
        35                  40                  45

Leu Val Thr Gly Ile Leu Trp Cys Val Asp Lys Phe Val Phe Ala Pro
 50                  55                  60

Lys Arg Arg Ala Arg Gln Ala Ala Ala Gln Thr Ala Ser Gly Asp Ala
 65                  70                  75                  80

Leu Asp Asn Ala Thr Leu Asn Lys Val Ala Pro Lys Pro Gly Trp Leu
            85                  90                  95

Glu Thr Gly Ala Ser Val Phe Pro Val Leu Ala Ile Val Leu Ile Val
           100                 105                 110

Arg Ser Phe Leu Tyr Glu Pro Phe Gln Ile Pro Ser Gly Ser Met Met
           115                 120                 125

Pro Thr Leu Leu Ile Gly Asp Phe Ile Leu Val Glu Lys Phe Ala Tyr
 130                 135                 140

Gly Ile Lys Asp Pro Ile Tyr Gln Lys Thr Leu Ile Glu Thr Gly His
145                 150                 155                 160

Pro Lys Arg Gly Asp Ile Val Val Phe Lys Tyr Pro Glu Asp Pro Lys
                165                 170                 175

Leu Asp Tyr Ile Lys Arg Ala Val Gly Leu Pro Gly Asp Lys Ile Thr
            180                 185                 190

Tyr Asp Pro Val Ala Lys Glu Val Thr Ile Gln Pro Gly Cys Ser Ser
        195                 200                 205

Gly Gln Ala Cys Glu Asn Ala Leu Pro Val Thr Tyr Ser Asn Val Glu
    210                 215                 220

Pro Ser Asp Phe Val Gln Thr Phe Ala Arg Arg Asn Gly Gly Glu Ala
225                 230                 235                 240

Thr Ser Gly Phe Phe Glu Val Pro Leu Asn Glu Thr Lys Glu Asn Gly
                245                 250                 255

Ile Arg Leu Thr Glu Arg Lys Glu Thr Leu Gly Asp Val Thr His Arg
            260                 265                 270

Ile Leu Met Val Pro Ile Ala Gln Asp Gln Leu Gly Met Tyr Tyr Gln
        275                 280                 285

Gln Pro Gly Gln Pro Leu Ala Thr Trp Val Val Pro Pro Gly Gln Tyr
    290                 295                 300

Phe Met Met Gly Asp Asn Arg Asp Asn Ser Ala Asp Ser Arg Tyr Trp
305                 310                 315                 320

Gly Phe Val Pro Glu Ala Asn Leu Val Gly Lys Ala Val Ala Ile Trp
                325                 330                 335
```

| Met | Ser | Phe | Asp | Lys | Gln | Glu | Gly | Glu | Trp | Pro | Thr | Gly | Val | Arg | Leu |
| | | | 340 | | | | | 345 | | | | | 350 | | |

| Ser | Arg | Ile | Gly | Gly | Ile | His |
| | | | 355 | | | |

( 2 ) INFORMATION FOR SEQ ID NO:5:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..93

( x i ) SEQUENCE DESCRIPTION: SEQ ID NO:5:

| GTG | AGA | AAG | AGT | TTA | ATT | ACA | CTT | GGT | TTG | GCT | TCC | GTC | ATC | GGG | ACA | 48 |
| Val | Arg | Lys | Ser | Leu | Ile | Thr | Leu | Gly | Leu | Ala | Ser | Val | Ile | Gly | Thr | |
| 1 | | | | 5 | | | | | 10 | | | | | 15 | | |

| AGC | AGT | TTT | TTG | ATC | CCA | TTT | ACA | AGT | AAA | ACT | GAG | TCG | ACC | GCC | | 93 |
| Ser | Ser | Phe | Leu | Ile | Pro | Phe | Thr | Ser | Lys | Thr | Glu | Ser | Thr | Ala | | |
| | | | 20 | | | | | 25 | | | | | 30 | | | |

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Val | Arg | Lys | Ser | Leu | Ile | Thr | Leu | Gly | Leu | Ala | Ser | Val | Ile | Gly | Thr |
| 1 | | | | 5 | | | | | 10 | | | | | 15 | |

| Ser | Ser | Phe | Leu | Ile | Pro | Phe | Thr | Ser | Lys | Thr | Glu | Ser | Thr | Ala |
| | | | 20 | | | | | 25 | | | | | 30 | |

( 2 ) INFORMATION FOR SEQ ID NO:7:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..96

( x i ) SEQUENCE DESCRIPTION: SEQ ID NO:7:

| ATG | TTG | AAG | AAA | GTC | ATT | TTA | TTA | TTG | GCT | GCA | GTC | CTA | CTT | CTC | TTA | 48 |
| Met | Leu | Lys | Lys | Val | Ile | Leu | Leu | Leu | Ala | Ala | Val | Leu | Leu | Leu | Leu | |
| 1 | | | | 5 | | | | | 10 | | | | | 15 | | |

| TTG | GCC | GCT | TTT | ATC | TTA | GTA | GGA | AGT | GAT | CCT | CTA | GAG | TCG | ACC | GCC | 96 |
| Leu | Ala | Ala | Phe | Ile | Leu | Val | Gly | Ser | Asp | Pro | Leu | Glu | Ser | Thr | Ala | |
| | | | 20 | | | | | 25 | | | | | 30 | | | |

( 2 ) INFORMATION FOR SEQ ID NO:8:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Leu | Lys | Lys | Val | Ile | Leu | Leu | Leu | Ala | Ala | Val | Leu | Leu | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ala | Ala | Phe | Ile | Leu | Val | Gly | Ser | Asp | Pro | Leu | Glu | Ser | Thr | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

( 2 ) INFORMATION FOR SEQ ID NO:9:

( i ) SEQUENCE CHARACTERISTICS:
        ( A ) LENGTH: 799 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 241..792

( x i ) SEQUENCE DESCRIPTION: SEQ ID NO:9:

```
GATCTAAAGA TTTTGCATAT GAGAACTCTC TTTCTTCTGA GTCCATCGCT TCTGAATTAT          60

GCGATTCATT TCTTTCAATA TTTTCAGGCC TAGTTATGAT CGACAAGAAA AAATAGGCAT         120

GATGTGGGTA AAGATGAAG ATTAACAGTT TGTAAAATCA CTTCAATGGT CCTAATGGGA          180

TTTTTTTTCG ATTCGTGATA ACATAAATTG AAGACCGTTG TTTATTGGAG GAAATCAGTT         240
```

| TTG | AAA | TCA | GAA | AAT | GTT | TCG | AAG | AAA | AAG | TCA | ATA | TTA | GAA | TGG | GCA | 288 |
|-----|-----|-----|-----|-----|-----|-----|-----|-----|-----|-----|-----|-----|-----|-----|-----|-----|
| Leu | Lys | Ser | Glu | Asn | Val | Ser | Lys | Lys | Lys | Ser | Ile | Leu | Glu | Trp | Ala |     |
| 1   |     |     |     | 5   |     |     |     |     | 10  |     |     |     |     | 15  |     |     |

| AAA | GCA | ATT | GTG | ATT | GCT | GTC | GTT | CTT | GCT | TTG | CTC | ATC | CGC | AAC | TTT | 336 |
|-----|-----|-----|-----|-----|-----|-----|-----|-----|-----|-----|-----|-----|-----|-----|-----|-----|
| Lys | Ala | Ile | Val | Ile | Ala | Val | Val | Leu | Ala | Leu | Leu | Ile | Arg | Asn | Phe |     |
|     |     |     | 20  |     |     |     |     | 25  |     |     |     |     | 30  |     |     |     |

| ATT | TTT | GCG | CCG | TAT | GTC | GTT | GAT | GGT | GAC | TCT | ATG | TAT | CCT | ACA | CTT | 384 |
|-----|-----|-----|-----|-----|-----|-----|-----|-----|-----|-----|-----|-----|-----|-----|-----|-----|
| Ile | Phe | Ala | Pro | Tyr | Val | Val | Asp | Gly | Asp | Ser | Met | Tyr | Pro | Thr | Leu |     |
|     |     |     | 35  |     |     |     |     | 40  |     |     |     |     | 45  |     |     |     |

| CAC | AAC | CGT | GAA | AGG | GTT | TTT | GTT | AAT | ATG | ACA | GTC | AAA | TAC | ATC | GGC | 432 |
|-----|-----|-----|-----|-----|-----|-----|-----|-----|-----|-----|-----|-----|-----|-----|-----|-----|
| His | Asn | Arg | Glu | Arg | Val | Phe | Val | Asn | Met | Thr | Val | Lys | Tyr | Ile | Gly |     |
|     |     | 50  |     |     |     |     | 55  |     |     |     |     | 60  |     |     |     |     |

| GAG | TTT | GAT | AGA | GGA | GAC | ATC | GTC | GTG | TTA | AAC | GGA | GAT | GAT | GTT | CAC | 480 |
|-----|-----|-----|-----|-----|-----|-----|-----|-----|-----|-----|-----|-----|-----|-----|-----|-----|
| Glu | Phe | Asp | Arg | Gly | Asp | Ile | Val | Val | Leu | Asn | Gly | Asp | Asp | Val | His |     |
| 65  |     |     |     |     | 70  |     |     |     |     | 75  |     |     |     |     | 80  |     |

| TAT | GTC | AAA | CGT | ATT | ATC | GGC | CTT | CCC | GGC | GAT | ACG | GTT | GAG | ATG | AAA | 528 |
|-----|-----|-----|-----|-----|-----|-----|-----|-----|-----|-----|-----|-----|-----|-----|-----|-----|
| Tyr | Val | Lys | Arg | Ile | Ile | Gly | Leu | Pro | Gly | Asp | Thr | Val | Glu | Met | Lys |     |
|     |     |     |     | 85  |     |     |     |     | 90  |     |     |     |     | 95  |     |     |

| AAT | GAC | CAG | CTC | TAT | ATC | AAC | GGG | AAA | AAG | GTG | GAC | GAA | CCT | TAT | TTG | 576 |
|-----|-----|-----|-----|-----|-----|-----|-----|-----|-----|-----|-----|-----|-----|-----|-----|-----|
| Asn | Asp | Gln | Leu | Tyr | Ile | Asn | Gly | Lys | Lys | Val | Asp | Glu | Pro | Tyr | Leu |     |
|     |     |     | 100 |     |     |     |     | 105 |     |     |     |     | 110 |     |     |     |

| GCG | GCT | AAT | AAA | AAG | AGA | GCG | AAA | CAG | GAC | GGT | TTT | GAC | CAT | TTG | ACC | 624 |
|-----|-----|-----|-----|-----|-----|-----|-----|-----|-----|-----|-----|-----|-----|-----|-----|-----|
| Ala | Ala | Asn | Lys | Lys | Arg | Ala | Lys | Gln | Asp | Gly | Phe | Asp | His | Leu | Thr |     |
|     |     | 115 |     |     |     |     | 120 |     |     |     |     | 125 |     |     |     |     |

| GAT | GAT | TTC | GGC | CCG | GTT | AAA | GTG | CCT | GAT | AAC | AAG | TAT | TTT | GTG | ATG | 672 |
|-----|-----|-----|-----|-----|-----|-----|-----|-----|-----|-----|-----|-----|-----|-----|-----|-----|
| Asp | Asp | Phe | Gly | Pro | Val | Lys | Val | Pro | Asp | Asn | Lys | Tyr | Phe | Val | Met |     |
|     | 130 |     |     |     |     | 135 |     |     |     |     | 140 |     |     |     |     |     |

| GGT | GAC | AAT | CGT | CGC | AAT | TCC | ATG | GAC | AGC | CGT | AAC | GGC | CTT | GGC | CTC | 720 |
|-----|-----|-----|-----|-----|-----|-----|-----|-----|-----|-----|-----|-----|-----|-----|-----|-----|
| Gly | Asp | Asn | Arg | Arg | Asn | Ser | Met | Asp | Ser | Arg | Asn | Gly | Leu | Gly | Leu |     |
| 145 |     |     |     |     | 150 |     |     |     |     | 155 |     |     |     |     | 160 |     |

| TTC | ACG | AAA | AAA | CAA | ATT | GCG | GGT | ACG | TCA | AAG | TTT | GTT | TTC | TAC | CCG | 768 |
|-----|-----|-----|-----|-----|-----|-----|-----|-----|-----|-----|-----|-----|-----|-----|-----|-----|
| Phe | Thr | Lys | Lys | Gln | Ile | Ala | Gly | Thr | Ser | Lys | Phe | Val | Phe | Tyr | Pro |     |
|     |     |     |     | 165 |     |     |     |     | 170 |     |     |     |     | 175 |     |     |

| TTT | AAC | GAA | ATG | CGC | AAA | ACA | AAT | TAGGATC | 799 |
|-----|-----|-----|-----|-----|-----|-----|-----|---------|-----|
| Phe | Asn | Glu | Met | Arg | Lys | Thr | Asn |         |     |
|     |     |     | 180 |     |     |     |     |         |     |

5,246,838

(2) INFORMATION FOR SEQ ID NO:10:

(i) SEQUENCE CHARACTERISTICS:
  (A) LENGTH: 184 amino acids
  (B) TYPE: amino acid
  (D) TOPOLOGY: linear (ii) MOLECULE TYPE: protein (xi) SEQUENCE DESCRIPTION: SEQ ID NO:10:

```
Leu Lys Ser Glu Asn Val Ser Lys Lys Ser Ile Leu Glu Trp Ala
 1               5                  10                  15

Lys Ala Ile Val Ile Ala Val Val Leu Ala Leu Leu Ile Arg Asn Phe
             20                  25                  30

Ile Phe Ala Pro Tyr Val Val Asp Gly Asp Ser Met Tyr Pro Thr Leu
             35                  40                  45

His Asn Arg Glu Arg Val Phe Val Asn Met Thr Val Lys Tyr Ile Gly
     50                  55                  60

Glu Phe Asp Arg Gly Asp Ile Val Leu Asn Gly Asp Asp Val His
 65                  70                  75              80

Tyr Val Lys Arg Ile Ile Gly Leu Pro Gly Asp Thr Val Glu Met Lys
             85                  90                  95

Asn Asp Gln Leu Tyr Ile Asn Gly Lys Lys Val Asp Glu Pro Tyr Leu
             100                 105                 110

Ala Ala Asn Lys Lys Arg Ala Lys Gln Asp Gly Phe Asp His Leu Thr
             115                 120                 125

Asp Asp Phe Gly Pro Val Lys Val Pro Asp Asn Lys Tyr Phe Val Met
     130                 135                 140

Gly Asp Asn Arg Arg Asn Ser Met Asp Ser Arg Asn Gly Leu Gly Leu
145                 150                 155                 160

Phe Thr Lys Lys Gln Ile Ala Gly Thr Ser Lys Phe Val Phe Tyr Pro
             165                 170                 175

Phe Asn Glu Met Arg Lys Thr Asn
             180
```

(2) INFORMATION FOR SEQ ID NO:11:

(i) SEQUENCE CHARACTERISTICS:
  (A) LENGTH: 181 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:11:

```
Glu Asn Val Ser Lys Lys Lys Ser Ile Leu Glu Trp Ala Lys Ala Ile
 1               5                  10                  15

Val Ile Ala Val Val Leu Ala Leu Leu Ile Arg Asn Phe Ile Phe Ala
             20                  25                  30

Pro Tyr Val Val Asp Gly Asp Ser Met Tyr Pro Thr Leu His Asn Arg
             35                  40                  45

Glu Arg Val Phe Val Asn Met Thr Val Lys Tyr Ile Gly Glu Phe Asp
     50                  55                  60

Arg Gly Asp Ile Val Val Leu Asn Gly Asp Asp Val His Tyr Val Lys
 65                  70                  75                  80

Arg Ile Ile Gly Leu Pro Gly Asp Thr Val Glu Met Lys Asn Asp Gln
             85                  90                  95

Leu Tyr Ile Asn Gly Lys Lys Val Asp Glu Pro Tyr Leu Ala Ala Asn
             100                 105                 110

Lys Lys Arg Ala Lys Gln Asp Gly Phe Asp His Leu Thr Asp Asp Phe
```

```
              115                        120                           125
   Gly Pro Val Lys Val Pro Asp Asn Lys Tyr Phe Val Met Gly Asp Asn
           130                        135                140

Arg Arg Asn Ser Met Asp Ser Arg Asn Gly Leu Gly Leu Phe Thr Lys
   145                     150                155                    160

Lys Gln Ile Ala Gly Thr Ser Lys Phe Val Phe Tyr Pro Phe Asn Glu
                       165                170                175

Met Arg Lys Thr Asn
                   180
```

( 2 ) INFORMATION FOR SEQ ID NO:12:

( i ) SEQUENCE CHARACTERISTICS:
        ( A ) LENGTH: 263 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
   Lys Lys Val Ala Pro Lys Pro Gly Trp Leu Glu Thr Gly Ala Ser Val
   1               5                   10                     15

Phe Pro Val Leu Ala Ile Val Leu Ile Val Arg Ser Phe Ile Tyr Glu
                   20                  25                 30

Pro Phe Gln Ile Pro Ser Gly Ser Met Met Pro Thr Leu Leu Ile Gly
               35                  40                 45

Asp Phe Ile Leu Val Glu Lys Phe Ala Tyr Gly Ile Lys Asp Pro Ile
           50                  55                 60

Tyr Gln Lys Thr Leu Ile Glu Asn Gly His Pro Lys Arg Gly Asp Ile
   65                      70                  75                  80

Val Val Phe Lys Tyr Pro Glu Asp Pro Lys Leu Asp Tyr Ile Lys Arg
                   85                  90                 95

Ala Val Gly Leu Pro Gly Asp Lys Val Thr Tyr Asp Pro Val Ser Lys
                   100                 105                110

Glu Leu Thr Ile Gln Pro Gly Cys Ser Ser Gly Gln Ala Cys Glu Asn
               115                 120                125

Ala Leu Pro Ala Thr Tyr Ser Asn Val Glu Pro Ser Asp Phe Val Gln
           130                 135                140

Thr Phe Ser Arg Arg Asn Gly Glu Ala Thr Ser Gly Phe Phe Glu
   145                     150                155                160

Val Pro Lys Asn Glu Thr Lys Glu Asn Gly Ile Arg Leu Ser Glu Arg
                   165                 170                175

Lys Glu Thr Leu Gly Asp Val Thr His Arg Ile Leu Thr Val Pro Ile
                   180                 185                190

Ala Gln Asp Gln Val Gly Met Tyr Tyr Gln Gln Pro Gly Gln Gln Leu
                   195                 200                205

Ala Thr Trp Ile Val Pro Pro Gly Gln Tyr Phe Met Met Gly Asp Asn
   210                     215                 220

Arg Asp Asn Ser Ala Asp Ser Arg Tyr Trp Gly Phe Val Pro Glu Ala
   225                     230                 235                240

Asn Leu Val Gly Arg Ala Thr Ala Ile Trp Met Ser Phe Asp Lys Gln
                   245                 250                255

Glu Gly Glu Trp Pro Thr Gly
                   260
```

( 2 ) INFORMATION FOR SEQ ID NO:13:

( i ) SEQUENCE CHARACTERISTICS:
        ( A ) LENGTH: 50 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:13:

| Leu | Ala | Leu | Leu | Ile | Arg | Asn | Phe | Ile | Phe | Ala | Pro | Tyr | Val | Val | Asp |
|-----|-----|-----|-----|-----|-----|-----|-----|-----|-----|-----|-----|-----|-----|-----|-----|
| 1 | | | | 5 | | | | | 10 | | | | | 15 | |

| Gly | Asp | Ser | Met | Tyr | Pro | Thr | Leu | His | Asn | Arg | Glu | Arg | Val | Phe | Val |
| | | | 20 | | | | | 25 | | | | | 30 | | |

| Asn | Met | Thr | Val | Lys | Tyr | Ile | Gly | Glu | Phe | Asp | Arg | Gly | Asp | Ile | Val |
| | | 35 | | | | | 40 | | | | | 45 | | | |

| Val | Leu |
| | 50 |

(2) INFORMATION FOR SEQ ID NO:14:

(i) SEQUENCE CHARACTERISTICS:
(A) LENGTH: 62 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:14:

| Ile | Val | Leu | Ile | Val | Arg | Ser | Phe | Ile | Tyr | Glu | Pro | Phe | Gln | Ile | Pro |
|-----|-----|-----|-----|-----|-----|-----|-----|-----|-----|-----|-----|-----|-----|-----|-----|
| 1 | | | | 5 | | | | | 10 | | | | | 15 | |

| Ser | Gly | Ser | Met | Met | Pro | Thr | Leu | Leu | Ile | Gly | Asp | Phe | Ile | Leu | Val |
| | | | 20 | | | | | 25 | | | | | 30 | | |

| Glu | Lys | Phe | Ala | Tyr | Gly | Ile | Lys | Asp | Pro | Ile | Tyr | Gln | Lys | Thr | Leu |
| | | 35 | | | | | 40 | | | | | 45 | | | |

| Ile | Glu | Asn | Gly | His | Pro | Lys | Arg | Gly | Asp | Ile | Val | Val | Phe |
| | | 50 | | | | | 55 | | | | | 60 | | | |

(2) INFORMATION FOR SEQ ID NO:15:

(i) SEQUENCE CHARACTERISTICS:
(A) LENGTH: 1314 base pairs
(B) TYPE: nucleic acid
(C) STRANDEDNESS: single
(D) TOPOLOGY: linear (xi) SEQUENCE DESCRIPTION: SEQ ID NO:15:

```
CTGCAGCAGG CATATAGTTT TCATCCAGAG TTTGGATCTA ACCAGCAAAA CTCTGTCTTA         60
CACAGGATGA CTTGGAATTA GAGTCCTTAT AGCAGAAAGA GCAGCAGGGC TGTCCTTGGG        120
TATCCGTTGC TCAGCCAAGT CATCAAATAA AAAGGATGAT TGCACAAGTG ACTATGTGT         180
CAATCTGTGG GTTTCTGCAT GCCAAGAGCC AGACCCTCCT CTGCGTCTGC TGGCCCAACC        240
CACCAAGGGA TGCTTTATTT AAACAGTTCC AAGTAGGGGA GACCAGCTGC CCCTGAACCC        300
CAGAACAACC AGCTGGATCA GTTCTCACAG GAGCTACAGC GCGGAGACTG GGTAAGTCAA        360
CGATCCCCAG AGCTGGGACA GAAGGGGCAG CAATGGGGCA GCAACTGAGG GAGAAGAGAG        420
CTGACGTTAG TGCTTAGGAG ACGTTGCACA CTTTGCAGAC AGGAAGTAAA GGAAATGGGA        480
CCCCAGAGTG GCCGCAGAGG GGCTGTGGGG TAAGACACTA CAGTGTGTGT CATAACCAAG        540
ACCCGATCAG GGAGTAGTTA CTTCTCTTCT TTTCTTACAG GAAACATGGT TCCAAAACTG        600
TTCACTTCCC AAATTTGTCT GCTTCTTCTG TTGGGGCTTC TGGCTGTGGA GGGCTCACTC        660
CATGTCAAAC CTCCACAGTT TACCTGGGCT CAATGGTTTG AAACCCAGCA CATCAATATG        720
ACCTCCCAGC AATGCACCAA TGCAATGCAG GTCATTAACA ATTATCAACG GCGATGCAAA        780
```

-continued

| | | | | | |
|---|---|---|---|---|---|
| AACCAAAATA | CTTTCCTTCT | TACAACTTTT | GCTAACGTAG | TTAATGTTTG | TGGTAACCCA | 840 |
| AATATGACCT | GTCCTAGTAA | CAAAACTCGC | AAAAATTGTC | ACCACAGTGG | AAGCCAGGTG | 900 |
| CCTTTAATCC | ACTGTAACCT | CACAACTCCA | AGTCCACAGA | ATATTTCAAA | CTGCAGGTAT | 960 |
| GCGCAGACAC | CAGCAAACAT | GTTCTATATA | GTTGCATGTG | ACAACAGAGA | TCAACGACGA | 1020 |
| GACCCTCCAC | AGTATCCGGT | GGTTCCAGTT | CACCTGGATA | GAATCATCTA | AGCTCCTGTA | 1080 |
| TCAGCACTCC | TCATCATCAC | TCATCTGCCA | AGCTCCTCAA | TCATAGCCAA | GATCCCATCT | 1140 |
| CTCCATATAC | TTTGGGTATC | AGCATCTGTC | CTCATCAGTC | TCCATACCCC | TTCAGCTTTC | 1200 |
| CTGAGCTGAA | GTGCCTTGTG | AACCCTGCAA | TAAACTGCTT | TGCAAATTCA | TCTGAAAGTG | 1260 |
| TCTGTGTGTC | TTCATTAGCC | GCTCTGCTGT | CATTTAGTGA | CAATCTACTC | TAGA | 1314 |

( 2 ) INFORMATION FOR SEQ ID NO:16:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Ile Val Val Val Leu Ser Gly Ser Met Glu Pro Ala Phe Gln Arg Gly
    1               5                   10                  15

Asp Ile Leu Phe Leu
                20

( 2 ) INFORMATION FOR SEQ ID NO:17:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

Ile Val Val Val Leu Ser Gly Ser Met Glu Pro Ala Phe His Arg Gly
    1               5                   10                  15

Asp Leu Leu Phe Leu
                20